United States Patent
Qiu et al.

(10) Patent No.: US 7,485,671 B2
(45) Date of Patent: *Feb. 3, 2009

(54) PROCESS FOR FORMING AN EMULSION USING MICROCHANNEL PROCESS TECHNOLOGY

(75) Inventors: Dongming Qiu, Dublin, OH (US); Anna Lee Tonkovich, Marysville, OH (US); Laura Silva, Dublin, OH (US); Richard Q. Long, Columbus, OH (US); Barry L. Yang, Dublin, OH (US); Kristina Marie Trenkamp, Dublin, OH (US)

(73) Assignee: Velocys, Inc., Plain City, OH (US)

( * ) Notice: Subject to any disclaimer, the term of this patent is extended or adjusted under 35 U.S.C. 154(b) by 427 days.

This patent is subject to a terminal disclaimer.

(21) Appl. No.: 10/440,056

(22) Filed: May 16, 2003

(65) Prior Publication Data
US 2004/0228882 A1 Nov. 18, 2004

(51) Int. Cl.
*B01F 3/08* (2006.01)
*B01F 17/00* (2006.01)
(52) U.S. Cl. .................. 516/53; 516/20; 516/924
(58) Field of Classification Search .......... 516/20, 516/53, 924
See application file for complete search history.

(56) References Cited

U.S. PATENT DOCUMENTS

| | | | |
|---|---|---|---|
| 3,489,690 A | 1/1970 | Lachampt et al. | 252/308 |
| 3,953,591 A * | 4/1976 | Snyder | 514/772.4 |
| 4,070,450 A * | 1/1978 | Barner et al. | 424/59 |
| 4,392,362 A | 7/1983 | Little | 62/514 |
| 4,516,632 A | 5/1985 | Swift et al. | 165/167 |
| 5,075,113 A | 12/1991 | DuBois | 424/450 |
| 5,309,637 A | 5/1994 | Moriarty | 29/890.054 |
| 5,317,805 A | 6/1994 | Hoopman et al. | 29/890.03 |
| 5,611,214 A | 3/1997 | Wegeng et al. | 62/498 |
| 5,727,618 A | 3/1998 | Mundinger et al. | 165/80.4 |
| 5,811,062 A | 9/1998 | Wegeng et al. | 422/129 |
| 5,858,314 A | 1/1999 | Hsu et al. | 422/211 |
| 6,126,723 A | 10/2000 | Drost et al. | 96/4 |

(Continued)

FOREIGN PATENT DOCUMENTS

EP 1 125 630 A2 8/2001

(Continued)

OTHER PUBLICATIONS

MAchine translation on www at JPO @ http://www19.ipdl.inpit.go.jp/PA1/cgi-bin/PA1INDEX for JP 11165062, pp. 1-7 of 7 (Jan. 2008).*

(Continued)

*Primary Examiner*—Daniel S Metzmaier
(74) *Attorney, Agent, or Firm*—Renner, Otto, Boisselle & Sklar, LLP

(57) ABSTRACT

The disclosed invention relates to a process for making an emulsion. The process comprises: flowing a first liquid through a process microchannel having a wall with an apertured section; flowing a second liquid through the apertured section into the process microchannel in contact with the first liquid, the second liquid being immiscible with the first liquid, the first liquid forming a continuous phase, and the second liquid forming a discontinuous phase dispersed in the first liquid.

31 Claims, 10 Drawing Sheets

U.S. PATENT DOCUMENTS

| | | | |
|---|---|---|---|
| 6,129,973 A | 10/2000 | Martin et al. | 428/166 |
| 6,155,710 A | 12/2000 | Nakajima et al. | 366/167.1 |
| 6,192,596 B1 | 2/2001 | Bennett et al. | 34/76 |
| 6,200,536 B1 | 3/2001 | Tonkovich et al. | 422/177 |
| 6,203,791 B1 | 3/2001 | Protopapa et al. | 424/94.64 |
| 6,216,343 B1 | 4/2001 | Leland et al. | 29/890.032 |
| 6,220,497 B1 | 4/2001 | Benz et al. | 228/118 |
| 6,230,408 B1 | 5/2001 | Ehrfeld et al. | 29/890.039 |
| 6,258,858 B1 | 7/2001 | Nakajima et al. | 516/73 |
| 6,281,254 B1 | 8/2001 | Nakajima et al. | 516/53 |
| 6,313,393 B1 | 11/2001 | Drost | 136/201 |
| 6,352,577 B1 | 3/2002 | Martin et al. | 96/4 |
| 6,381,846 B2 | 5/2002 | Insley et al. | 29/890.039 |
| 6,387,301 B1 * | 5/2002 | Nakajima et al. | 264/4.4 |
| 6,415,860 B1 | 7/2002 | Kelly et al. | 165/748 |
| 6,431,695 B1 | 8/2002 | Johnston et al. | 347/86 |
| 6,457,854 B1 | 10/2002 | Koop et al. | 366/336 |
| 6,488,838 B1 | 12/2002 | Tonkovich et al. | 208/108 |
| 6,540,975 B2 | 4/2003 | Tonkovich et al. | 423/659 |
| 6,546,998 B2 | 4/2003 | Oh et al. | 165/110 |
| 6,576,023 B2 * | 6/2003 | Nakajima et al. | 264/14 |
| 6,675,875 B1 | 1/2004 | Vafai et al. | 165/80.4 |
| 6,746,819 B1 | 6/2004 | Schmitz et al. | 430/272.1 |
| 6,747,178 B1 | 6/2004 | Harston et al. | 570/175 |
| 6,749,814 B1 | 6/2004 | Bergh et al. | 422/130 |
| 6,749,817 B1 | 6/2004 | Mulvaney, III | 422/200 |
| 6,755,211 B1 | 6/2004 | O'Connor et al. | 137/554 |
| 6,769,444 B2 | 8/2004 | Guzman et al. | 137/15.01 |
| 6,770,245 B2 | 8/2004 | Akporiaye et al. | 422/82.12 |
| 6,773,684 B2 | 8/2004 | Lesieur et al. | 422/198 |
| 6,916,113 B2 | 7/2005 | Van de Goor et al. | 366/108 |
| 6,935,768 B2 | 8/2005 | Lowe et al. | 366/167.1 |
| 6,935,772 B2 | 8/2005 | Karp et al. | 366/341 |
| 6,969,746 B2 | 11/2005 | Krull et al. | 526/64 |
| 7,001,576 B2 | 2/2006 | Hohmann et al. | 422/224 |
| 7,378,473 B2 | 5/2008 | Torii | |
| 2002/0071797 A1 | 6/2002 | Loffler et al. | 422/190 |
| 2003/0027858 A1 | 2/2003 | Lambert et al. | 514/458 |
| 2003/0190563 A1 | 10/2003 | Nagasawa et al. | 430/569 |
| 2004/0011413 A1 | 1/2004 | Fuji et al. | 137/896 |
| 2004/0027915 A1 | 2/2004 | Lowe et al. | 366/341 |
| 2004/0029977 A1 | 2/2004 | Kawa et al. | 514/786 |
| 2004/0037161 A1 | 2/2004 | Honda et al. | 366/176.1 |
| 2004/0104010 A1 | 6/2004 | Kenny et al. | 165/80.4 |
| 2004/0123626 A1 | 7/2004 | Caze et al. | 65/17.2 |
| 2004/0125689 A1 | 7/2004 | Ehrfeld et al. | 366/165.1 |
| 2004/0130057 A1 | 7/2004 | Mehrabi et al. | 264/171.13 |
| 2004/0131345 A1 | 7/2004 | Kylberg et al. | 392/465 |
| 2004/0131507 A1 | 7/2004 | Saitmacher et al. | 422/111 |
| 2004/0131829 A1 | 7/2004 | Joseph et al. | 428/166 |
| 2004/0136902 A1 | 7/2004 | Plath et al. | 423/651 |
| 2004/0141893 A1 | 7/2004 | Martin | 422/198 |
| 2004/0143059 A1 | 7/2004 | Cabrera | 524/800 |
| 2004/0144421 A1 | 7/2004 | Parce et al. | 137/14 |
| 2004/0156762 A1 | 8/2004 | Schuppich et al. | 422/191 |
| 2005/0152690 A1 | 7/2005 | Nagasawa et al. | 396/142 |
| 2005/0161326 A1 | 7/2005 | Morita et al. | 204/450 |
| 2005/0233040 A1 | 10/2005 | Ehrfeld et al. | 426/518 |
| 2005/0279491 A1 | 12/2005 | Thome et al. | 165/272 |
| 2006/0077755 A1 | 4/2006 | Higuchi et al. | 366/336 |
| 2006/0121122 A1 | 6/2006 | Nakajima et al. | 424/490 |
| 2006/0128815 A1 | 6/2006 | Clare et al. | 516/9 |

FOREIGN PATENT DOCUMENTS

| | | |
|---|---|---|
| EP | 1 311 341 B1 | 8/2001 |
| EP | 0 904 608 B1 | 12/2001 |
| EP | 1 171 227 B1 | 6/2003 |
| EP | 1 382 382 A1 | 7/2003 |
| EP | 1 362 634 A1 | 11/2003 |
| EP | 1 180 062 B1 | 3/2004 |
| EP | 1 390 131 B1 | 7/2005 |
| EP | 1 510 251 B1 | 6/2006 |
| EP | 1 289 660 B1 | 8/2006 |
| JP | 5279523 | 10/1992 |
| JP | 11-165062 * | 6/1999 |
| WO | 97/32687 | 9/1997 |
| WO | WO 98/30205 * | 7/1998 |
| WO | 98/55812 | 12/1998 |
| WO | 00/06295 | 2/2000 |
| WO | 01/10773 A1 | 2/2001 |
| WO | 01/12312 A2 | 2/2001 |
| WO | 01/43857 A1 | 6/2001 |
| WO | 01/54807 A1 | 8/2001 |
| WO | 01/95237 A2 | 12/2001 |
| WO | WO 02/28769 * | 4/2002 |
| WO | 03/026788 | 4/2003 |
| WO | 03/068381 A1 | 8/2003 |
| WO | 03/078052 A1 | 9/2003 |
| WO | 03/106386 A2 | 12/2003 |
| WO | 2004/043580 | 5/2004 |
| WO | 2004/045760 | 6/2004 |
| WO | 2004/050799 | 6/2004 |
| WO | 2004/052518 | 6/2004 |
| WO | 2004/052530 | 6/2004 |
| WO | 2004/052941 | 6/2004 |
| WO | 2004/054013 | 6/2004 |
| WO | 2004/054696 | 7/2004 |
| WO | 2004/062790 | 7/2004 |
| WO | 2004/062792 | 7/2004 |
| WO | 2004/162791 | 7/2004 |
| WO | 2004/067160 | 8/2004 |
| WO | 2004/067444 | 8/2004 |
| WO | 2004/067708 | 8/2004 |
| WO | 2005/058477 A1 | 6/2005 |
| WO | 2005/063368 A2 | 7/2005 |
| WO | 2005/077508 A1 | 8/2005 |
| WO | 2005/079964 A1 | 9/2005 |

OTHER PUBLICATIONS

Matlosz et al.; "Microreactors as Tools in Chemical Research"; Microreaction Technology; IMRET 5: Proceedings of the Fifth International Conference on Microreaction Technology (May 27-30, 2001).

Srinivasn et al.; "Micromachined Reactors for Catalytic Partial Oxidation Reactions"; AIChE Journal; Nov. 1997; vol. 43, No. 11; pp. 3059-3069.

TeGrotenhuis et al.; Optimizing Microchannel Reactors by Trading-Off Equilibrium and Reaction Kinetics through Temperature Management; Prepared for presentation at IMRET 6—6th International Conference on Microreaction Technology; Mar. 10-14, 2002.

Rostami et al.; "Flow and Heat Transfer for Gas Flowing in Microchannels: a Review"; Heat and Mass Transfer 38 (2002) 359-367, month unknown.

Dow Chemical Co.; Dow Dispersion Sciences, Advanced Emulsions through Advanced Science, Improving the Aesthetics of Personal Care Formulations; Published Mar. 2003.

Dow Chemical Co.; Dow Dispersion Sciences, Advanced Emulsions through Advanced Science, A New Approach to Creating Uniquely Functional Cosmetic Formulations; Published Mar. 2003.

Dow Chemical Co.; Dow Dispersion Sciences, Advanced Emulsions through Advanced Science, Creating New Ways for Personal Care Manufacturers to Optimize Operational Efficiency; Published Mar. 2003.

"Preparation of Emulsions Using Porous Membranes in Membrane Contactor"; IGVT Universitat Stuttgart Fraunhofer-Gessellschaft; www.igb.fraunhofer.de/WWW/GF/DP/en/GFDP_22_Emulgieren.en.html, (Copyright 2002)(Apr. 16, 2003).

Schroder et al.; "Effect of Dynamic Interfacial Tension on the Emulsification Process Using Microporous, Ceramic Membranes"; Journal of Colloid and Interface Science 202, 334-340 (1998).

Beauty-Inn AG, Intensiv-Kosmetikinstitut; Sauerstoff-Spruhkosmetik; www.beauty-inn.ch/Behandlung-Sauerstoff-Spruehkosmetik.htm. (Nov. 2001).

Peng et al.; "Controlled Production of Emulsion Using a Crossflow Membrane"; PACE University of Exeter; www.pace.leeds.ac.uk/projects/p94x7.htm., (Nov. 6, 1997).

nst News; International Activities in Microsystem Technology; Microfluidic Systems New Products; No. 17, Jul./Aug. 1996.

Kawakatsu et al.; Production of W/O/W Emulsions and S/O/W Pectin Microcapsules by Microchannel Emulsification; Colloids and Surfaces; A: Physicochemical and Engineering Aspects 189 (2001) 257-264, month unknown.

Tenore; "Surfactant-Free Emulsion Systems"; Cosmetic Science & Business 2000; www.atalink.co.uk/csb2000/html/art_rawmats_lipo.htm., (Oct. 30, 2002).

Lin; "Low-Surfactant Emulsification"; J. Soc. Cosmet. Chem., 30, 167-180 (May/Jun. 1979).

Friberg et al.; Emulsions; Kirk-Othmer Encyclopedia of Chemical Technology; (Dec. 4, 2000) www.mrw.interscience.wiley.com/kirk/articles/emulfrib.a01/sect12.html., (Aug. 7, 2002).

Umbanhowar et al.; "Monodisperse Emulsion Generation via Drop Break Off in A Coflowing Stream"; Langmuir 2000, 16, 347-351, month unknown.

Gneist et al.; "Droplet Formation in Liquid/Liquid Systems Using High Frequency AC Fields"; Chem-Eng. Technol. 25 (2002) 2; pp. 129-133, month unknown.

Vladisavljevic et al.; "Preparation and Analysis of Oil-in-Water Emulsions with a Narrow Droplet Size Distribution using Shirasu-porous-glass (SPG) Membranes"; Presented at the International Congress on Membranes and Membrane Processes (ICOM), Toulouse, France, Jul. 7-12, 2002, month unknown.

Sugiura et al.; "Characterization of Spontaneous Transformation-Based Droplet Formation During Microchannel Emulsification"; J. Phys. Chem B, 2002, 106, 9405-9409, month unknown.

Tong et al.; "Surfactant Effect on Production of Monodispersed Microspheres by Microchannel Emulsification Method"; Journal of Surfactants and Detergents, vol. 3, No. 3 (Jul. 2000).

Rudhardt et al.; "Phase switching of ordered arrays of liquid crystal emulsions"; Applied Physics Letters, vol. 82, No. 16; Apr. 21, 2003, pp. 2610-2612.

Besser, Ronald S. "New Directions in Reactor Design Through Miniaturization". Sep. 13, 2002, Tulane Engineering Forum, pp. 1-26.

International Search Report and Written Opinion, Application No. PCT/US2004/014736, mailed Mar. 7, 2004.

Written Opinion of the International Preliminary Examining Authority; International Application No. PCT/US2004/014736; mailed Aug. 19, 2005.

Iwamoto et al.; "Preparation of Gelatine Microbeads With a Narrow Size Distribution Using Microchannel Emulsification"; AAPS PharmSciTech 2002; 3 (3) article 25, month unknown.

Nakajima; "Novel Microchannel System for Monodispersed Microspheres"; RIKEN Review No. 35 (Jun. 2001); Focused on Science and Technology in Micro/Nano Scale; pp. 21-23.

Invitation to Pay Additional Fees and Partial International Search Report, Application No. PCT/US2004/014736, mailed Nov. 25, 2004.

International Report on Patentability, Application No. PCT/US2004/014736, mailed Sep. 29, 2005.

Nakajima; "Novel microchannel system for monodispersed microspheres"; RIKEN Review No. 36 (Jun. 2001); Focused on Science and Technology in Micro/Nan Scale; pp. 21-23.

Lambrich et al,; "Emulsification using microporous systems"; Journal of Membrane Science 257; pp. 76-84, (available online Apr. 2005).

Kiwi-Minsker, et al.; "Microstructured reactors for catalytic reactions"; Catalysis Today 110; pp. 2-14, (available online Oct. 2005).

Priest, et al.; "Generation of monodisperse gel emulsions in a microfluidic device"; Applied Physics Letters 88, 024106 (available online Jan. 2006).

Chambers et al.; "Elemental fluorine Part 13, Gas-liquid thin film microreactors for selective direct fluorination"; Lab on a Chip, 2001, 1, 132-137.

Chambers et al.; "Elemental fluorine Part 16. Versatile thin-film-gas-liquid multi-channel microreactors for effective scale-out"; Lab Chip; 2005, 5, 191-198.

Chambers et al. "Elemental fluorine Part 18. Selective direct fluorination of 1,3-ketoesters and 1,3-diketones using gas/liquid microreactor technology"; Lab Chip, 2005, 5, 1132-1139, month unavailable.

Chambers et al.; "Versatile Gas/Liquid Microreactors for Industry"; Chem. Eng. Technol., 2005, 28, No. 3, pp. 344-352, month unavailable.

Commenge et al.; "Gas-phase residence time distribution in a falling-film microreactor"; Chemical Engineering Science 61, 2006, 597-604, available online Sep. 1, 2005.

de Bellefon et al.; "Asymmetric catalytic hydrogenations at microlitre scale ina helicoidal single channel falling film micro-reactor"; Catalysis Today 110 (2005), pp. 179-187, available online Oct. 24, 2005.

Doku et al.; "On-microchip multiphase chemistry—a review of microreactor design principles and reagent contacting modes"; Tetrahedron 61 (2005), pp. 2733-2742.

Gunther et al.; "Transport and reaction in microscale segmented gas-liquid flow"; Lab Chip, 2004, 4, pp. 278-286, first published on the web Jun. 16, 2004.

Haverkamp et al.; "Characterization of a Gas/Liquid Microreactor, the Micro Bubble Column: Determination of Specific Interfacial Area"; International Conference on Microreaction Technology, 2001, pp. 202-214.

Heibel et al.; "Flooding Performance of Square Channel Monolith Structures"; Ind. Eng. Chem. Res. 2002, 41, pp. 6759-6771.

Heibel et al.; "Gas and liquid phase distribution and their effect on reactor performance in the monolith film flow reactor"; Chemical Engineering Science 56 (2001), pp. 5935-5944.

Heibel et al.; "Improving Flooding Performance for Countercurrent Monolith Reactors"; Ind. Eng. Chem. Res. 2004, 43, pp. 4848-4855.

Heibel et al.; "Influence of channel geometry on hydrodynamics and mass transfer in the monolith film flow reactor"; Catalysis Today 69 (2001), pp. 153-163.

Hessel et al.; "Gas-Liquid and Gas-Liquid-Solid Microstructured Reactors: Contacting Principles and Applications"; Ind. Eng. Chem. Res. 2005, 44, pp. 9750-9769.

Hessel et al.; "Gas/Liquid Microreactors for Direct Fluorination of Aromatic Compounds using Elemental Fluorine"; International Conference on Microreaction Technology, 2000, pp. 526-548.

Hessel et al.; "Gas/Liquid Microreactors: Hydrodynamics and Mass Transfer"; International Conference on Microreaction Technology, 2000, pp. 174-186.

Hessel et al.; "Microchemical Engineering: Components, Plant Concepts, User Acceptance—Part II"; Chem. eng. Technol. 26 (2003) 4.

Jahnisch et al.; "Direct fluorination of toluene using elemental fluorine in gas/liquid microreactors"; Journal of Fluorine Chemistry 105 (2000), pp. 117-128.

Khinast et al.; "Reactive mass transfer at gas-liquid interfaces: impact of micro-scale fluid dynamics on yield and selectivity of liquid-phase cyclohexane oxidation"; Chemical Engineering Science 58 (2003), pp. 3961-3971.

Kiwi-Minsker et al.; "Microstructured reactors for catalytic reactions"; Catalysis Today 110 (2005), pp. 2-14.

Koynov et al.; "Micromixing in Reactive, Deformable Bubble, and Droplet Swarms"; Chem. Eng. Technol. 2006, 29, No. 1, pp. 13-23.

Kreutzer et al.; "Multiphase monolith reactors: Chemical reaction engineering of segmented flow in microchannels"; Chemical Engineering Science 60 (2005), pp. 5895-5916.

Liu et al.; "Gas-Liquid Catalytic Hydrogenation Reaction in Small Catalyst Channel"; AIChE Journal, Aug. 2005, vol. 51, No. 8, pp. 2285-2297.

Losey et al.; "Design and Fabrication of Microfluidic Devices for Multiphase Mixing and Reaction"; Journal of Microelectromechanical Systems, vol. 11, No. 6, Dec. 2002, pp. 709-717.

Losey et al.; "A Micro Packed-Bed Reactor for Chemical Synthesis"; Department of Chemical Engineering, Massachusetts Institute of Technology; International Conference on Microreaction Technology, 2000, pp. 277-285.

Losey et al.; "Microfabricated Devices for Multiphase Catlytic Processes"; Department of Chemical Engineering, Massachusetts Institute of Technology, International Conference on Microreaction Technology, 2000, pp. 416-422.

Losey et al.; "Microfabricated Multiphase Packed-Bed Reactors: Characterization of Mass Transfer and Reactions"; *Ind. Eng. Chem. Res.* 2001, 40, pp. 2555-2562.

Lowe et al.; "Micromixing Technology"; International Conference on Microreaction Technology, 2000, pp. 31-48.

Meille et al,; "Gas/Liquid Mass Transfer in Small Laboratory Batch Reactors: Comparison of Methods"; *Ind. Eng. Chem. Res.* 2004, 43, pp. 924-927.

Pestre et al.; "Effect of gas-liquid mass transfer on enantioselectivity in asymmetric hydrogenations"; *Journal of Molecular Catalysis A: Chemical* 252 (2006), pp. 85-89.

Roy et al.; "Design of monolithic catalysts for multiphase reactions"; *Chemical Engineering Science* 59 (2004), pp. 957-966.

Roy et al.; "Monoliths as Multiphase Reactors: A Review"; *AIChE Journal*, Nov. 2004, vol. 50, No. 11, pp. 2918-2938.

Yeong et al.; "Catalyst preparation and deactiviation issues for nitrobenzene hydrogenation in a microstructured falling film reactor"; *Catalysis Today* 81 (2003), pp. 641-651.

Yeong et al.; "Experimental studies of nitrobenzene hydrogenation in a microstructured falling film reactor"; *Chemical Engineering Science* 59 (2004), pp. 3491-3493.

Abdallah et al.; "Gas-Liquid and gas-liquid-solid catalysts in a mesh microreactor"; *Chem. Commun.*, 2004, pp. 372-373; First published on the web Jan. 22, 2004.

Angeli et al.; "Modelling of Gas-Liquid Catalytic Reactions in Microchannels"; International Conference on Microreaction Technology (2000), pp. 253-259.

Besser; Stevens Institute of Technology; A Look at Microchemical Systems (Feb. 23, 2006), pp.1-21.

Boger; "Monolithic Catalysts for the Chemical Industry"; *Ind. Eng. Chem. Res.*, 2004, 43, 4602-4611.

Office Action, U.S. Appl. No. 10/844,061, mailed Jun. 6, 2005.

Office Action, U.S. Appl. No. 10/844,061, mailed Jan. 29, 2007.

Office Action, U.S. Appl. No. 10/844,061, mailed Nov. 8, 2006.

Notice of Allowance mailed Sep. 20, 2007, U.S. Appl. No. 10/844,061.

Office Action, U.S. Appl. No. 10/844,061, mailed Jun. 6, 2007.

Ouyang et al.; "Flexible Microreactor System for Chemical Research at Moderate and High Temperatures"; Stevens Institute of Technology.

Wegeng et al.; "Compact Fuel Processors for Fuel Cell Powered Automobiles Based on Microchannel Technology"; Fuel Cells Bulletin No. 28; pp. 8-13.

McGovern et al.; "Catalyst Trap Microreactor for Hydrogenation of a Pharmaceutical Intermediate"; Stevens Institute of Technology.

McGovern et al.; "Flow Regimes in a Catalyst Trap Microreactor"; Stevens Institute of Technology.

Utada et al.; "Monodisperse Double Emulsions Generated from a Microcapillary Device"; *Science*, vol. 308, Apr. 22, 2005.

* cited by examiner

PROCESS FOR FORMING AN EMULSION USING MICROCHANNEL PROCESS TECHNOLOGY

TECHNICAL FIELD

This invention relates to a method for making an emulsion using microchannel process technology.

BACKGROUND OF THE INVENTION

An emulsion is formed when two immiscible liquids, usually water or a water-based solution and a hydrophobic organic liquid (e.g., an oil) are mixed so that one liquid forms droplets in the other liquid. Either of the liquids can be dispersed in the other liquid. When, for example, oil is dispersed in water, the emulsion is referred to as an oil-in-water (o/w) emulsion. The reverse case is a water-in-oil (w/o) emulsion.

If the emulsion is not stabilized by using certain methods, typically by adding surfactants or emulsifiers, the emulsion tends to agglomerate, form a creaming layer, coalesce, and finally separate into two phases. If a surfactant or emulsifier (sometimes referred to as a surface-active agent) is added to one or both of the immiscible liquids, one of the liquids forms a continuous phase and the other liquid remains in droplet form ("disperse or dispersed phase"), the droplets being dispersed in the continuous phase. On the other hand, the degree of stability without a surfactant is increased when droplet size is decreased below certain values. For example, a typical o/w emulsion of a droplet size of 20 microns may be only temporally stable (hours) while that of 1 micron may be considered as "quasi-permanently" stable (weeks or longer). However, the energy consumption and the power requirement for the emulsification system and process are drastically increased for smaller droplet size in conventional mixing and agitation hardware, especially for highly viscous emulsions of very small droplet size and large output. It has been observed that the doubling of energy dissipation (energy consumption) only causes a reduction of average droplet size of 25%. Shear force is usually applied to overcome the surface tension force of the dispersed phase and in turn to breakup larger droplets into smaller ones. It is known that as the size of the droplet size decreases, the surface tension required to keep the droplet shape increases. Energy consumption takes place in various forms, for example, it can be the energy needed by the stirrer to overcome shear force of the emulsion in a batch process, the energy for heating and cooling, and/or the power to overcome pressure drop in a continuous process. Heating is often needed for emulsification when one of the phases does not flow at room temperature. A heated emulsion has lower stability, however, due to lower viscosity of the continuous phase and in turn less drag. Drag is necessary to stop the motion of the droplets and in turn the coalescence. After emulsification, droplets tend to rise by buoyancy. As such, an immediate cooling down is usually needed, which also consumes energy.

The type of emulsion (o/w or w/o) may be determined by the volume ratio of the two liquids provided the ratio is relatively high. For example, with 5% water and 95% oil (an w/o phase ratio of 0.0526), the emulsion will typically become w/o unless measures are taken to provide for the formation of an o/w emulsion. However, for a uniform droplet size of volumetrical ratio between 0.26% and 74% both o/w and w/o emulsions are possible. For non-uniform droplet size distribution this range of ratio could be larger.

For moderate phase ratios (>0.333), the type of emulsion may be decided by several factors, such as order of addition or type of surfactant. One liquid slowly added to the other with agitation usually results in the last-mentioned liquid being the continuous phase. Another factor is preferred solubility of the surfactant; the phase in which the surfactant is soluble typically is continuous.

Occasionally, inversion takes place; an o/w emulsion changes into w/o emulsion or vice versa. More complex emulsions such as double emulsions may be formed when the water droplets in a continuous oil phase themselves contain dispersed oil droplets. Such oil-in-water-in-oil emulsions are noted as o/w/o. In the same manner a w/o/w emulsion may be formed.

A problem with many of the emulsions that are currently available relates to the presence of surfactants or emulsifiers in their formulations, or at least relatively high concentrations of such surfactants or emulsifiers. These surfactants or emulsifiers are required in order to stabilize the emulsions, but are undesirable for many applications. For example, heating without bubbling or boiling is often desired in emulsification processes, however it is found that the onset temperature of nucleate boiling or air bubble formation from dissolved air in the continuous phase lowers when surfactants or emulsifiers are present. Boiling may cause unwanted property changes. Air bubbles cause more creaming and other undesired features. Another example relates to the fact that low-surfactant or surfactant free emulsions are highly desirable for skin care products in the cosmetic industry. A major disadvantage of some surfactants or emulsifiers is their tendency to interact with preservatives such as the esters of p-hydroxybenzoic acid. Skin irritation is another problem often associated with the use of surfactants or emulsifiers. Many adverse skin reactions experienced by consumers from the use of cosmetics are directly related to the presence of the surfactants or emulsifiers. Another example relates to the problem with using surfactants wherein water proofing is desired. For example, in water-based paints, as well as certain skin care products such as sunscreen, the active ingredient is not waterproof due to the presence of water-soluble surfactants. The inventive process provides a solution to this problem.

A problem relating to the use of many pharmaceutically acceptable compounds or drugs relates to the fact that they are insoluble or poorly soluble in water and there are limitations as to the surfactants or emulsifiers that may be used. This has resulted in the discovery of drugs that are not clinically acceptable due to problems relating to transporting the drugs into the body. Emulsion formulation problems are particularly problematic with drugs for intravenous injection and the administration of chemotherapeutic or anti-cancer agents. This invention provides a solution to this problem.

The inventive process involves making emulsions using microchannel process technology. In one embodiment, the process requires relatively low energy consumption and provides for low continuous phase pressure drop and low pressure drop between the bulk dispersion phase and the continuous phase. The emulsions made using this process, at least in one embodiment, are characterized by a dispersed phase with a relatively small and relatively uniform droplet size. These emulsions exhibit a high degree of stability as a result of the small droplet size and the controlled droplet size distribution in the dispersed phase. This creates the potential for making low-surfactant or surfactant-free emulsions which are desirable for many applications, including skin care products in the cosmetic industry.

SUMMARY OF THE INVENTION

This invention relates to a process for making an emulsion, comprising: flowing a first liquid through a process microchannel having a wall with an apertured section; flowing a second liquid through the apertured section into the process microchannel in contact with the first liquid, the second liquid being immiscible with the first liquid, the first liquid forming a continuous phase, and the second liquid forming a discontinuous phase dispersed in the first liquid.

BRIEF DESCRIPTION OF THE DRAWINGS

In the annexed drawings, like parts and features have like references.

DETAILED DESCRIPTION OF THE INVENTION

The term "microchannel" refers to a channel having at least one internal dimension of height or width of up to about 10 millimeters (mm), and in one embodiment up to about 5 mm, and in one embodiment up to about 2 mm, and in one embodiment up to about 1 mm. In one embodiment, the height or width is in the range of about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.75 mm, and in one embodiment about 0.05 to about 0.5 mm. Both height and width are perpendicular to the direction of flow through the microchannel.

The term "adjacent" when referring to the position of one channel relative to the position of another channel means directly adjacent such that a wall separates the two channels. This wall may vary in thickness. However, "adjacent" channels are not separated by an intervening channel that would interfere with heat transfer between the channels.

The term "immiscible" refers to one liquid not being soluble in another liquid or only being soluble to the extent of up to about 1 milliliter per liter at 25° C.

The term "water insoluble" refers to a material that is insoluble in water at 25° C., or soluble in water at 25° C. up to a concentration of about 0.1 gram per liter.

Figure 1:
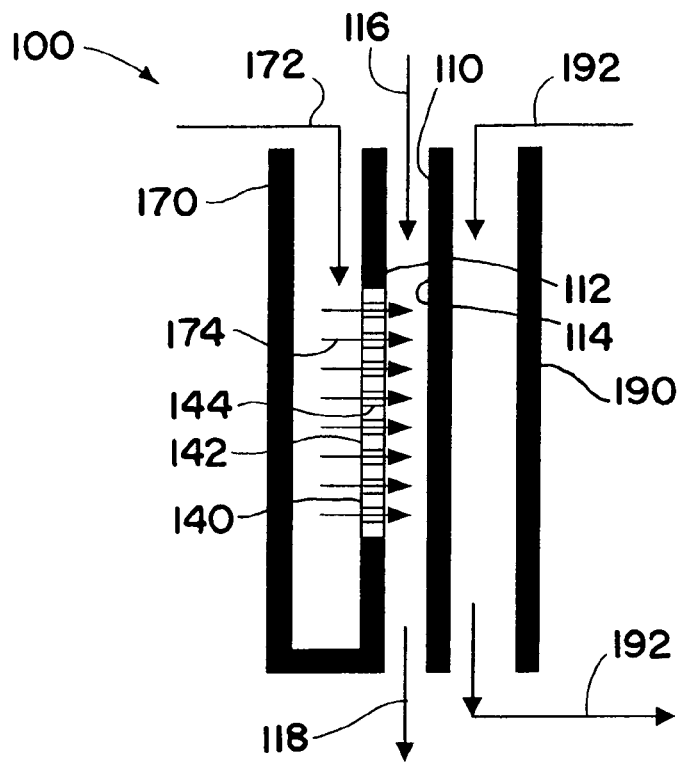
FIG. 1 is a flow sheet illustrating the inventive process in a particular form wherein a first liquid flows through a process microchannel and is mixed with a second liquid that flows through an apertured section in the process microchannel.

The inventive process will be initially described with reference to FIG. 1. Referring to FIG. 1, the inventive process is conducted in emulsion forming unit 100 which comprises process microchannel 110 which has opposite sidewalls 112 and 114, and an apertured section 140 in sidewall 112. The apertured section 140 may be referred to as a porous section or porous substrate. Adjacent to the sidewall 112 is liquid channel 170 which opens to process microchannel 110 through apertured section 140. Adjacent to sidewall 114 is heat exchange channel 190. In operation, a first liquid flows through microchannel 110, as indicated by directional arrow 116. A second liquid flows into liquid channel 170, as indicated by directional arrow 172, and then flows through apertured section 140, as indicated by directional arrows 174, into process microchannel 110. In process microchannel 110, the second liquid contacts and mixes with the first liquid to form an emulsion. The second liquid forms a discontinuous phase within the first liquid. The first liquid forms a continuous phase. The emulsion flows out of the process microchannel 110, as indicated by directional arrow 118. The emulsion may be a water-in-oil emulsion or an oil-in-water emulsion. Heat exchange fluid flows through the heat exchange channel 190, as indicated by directional arrows 192, and heats or cools the liquids in the process microchannel 110.

Although only a single emulsion forming unit 100 is illustrated in FIG. 1, there is practically no upper limit to the number of emulsion forming units 100 that may be used in the inventive process. For example, one, two, three, four, five, six, eight, ten, twenty, fifty, one hundred, hundreds, one thousand, thousands, ten thousand, tens of thousands, one hundred thousand, hundreds of thousands, millions, etc., of the emulsion forming units 100 may be used. The process microchannels 110, and associated liquid channels 170 and heat exchange channels 190, may be arranged in parallel, for example, in arrays of planar microchannels. The process microchannels 110 may be aligned in parallel in one plane, the liquid channels 170 may be aligned in parallel in an adjacent plane on one side of the process microchannels 110, and the heat exchange channels 190 may be aligned in parallel in another plane on the other side of the process microchannels 110. These emulsion forming units 100 have appropriate headers, footers, valves, conduit lines, tubings, control mechanisms, etc., to control the input and output of process liquids and heat exchange fluids which are not shown in FIG. 1, but can be provided by those skilled in the art. For example, at the inlet and outlet of the emulsification section sloped headers and footers may be used for connecting the conduit lines or tubings to avoid unnecessary pressure drops associated with the size of the process microchannels.

Each of the process microchannels 110 may have a cross section that has any configuration, for example, square, rectangular, circular, oval, trapezoidal, etc. Each of the process microchannels has at least one internal dimension of height or width of up to about 10 mm, and in one embodiment from about 0.05 to about 10 mm, and in one embodiment about 0.001 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.5 mm. The other internal dimension of height or width may be of any value, for example, it may range from about 0.01 cm to about 100 cm, and in one embodiment from about 0.01 to about 75 cm, and in one embodiment from about 0.1 to about 50 cm, and in one embodiment about 0.2 cm to about 25 cm. The length of each of the process microchannels 110 may be of any value, for example, it may range from about 0.1 to about 500 cm, and in one embodiment about 0.1 to about 250 cm, and in one embodiment about 1 to about 100 cm, and in one embodiment about 1 cm to about 50 cm, and in one embodiment about 2 to about 25 cm.

The liquid channels 170 may be microchannels although they may have larger dimensions that would not characterize them as microchannels. Each of these channels may have a cross section that has any configuration, for example, square, rectangular, circular, oval, trapezoidal, etc. Each channel may have an internal dimension of height or width of up to about 10 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. The other internal dimension may range from about 1 mm to about 1 m, and in one embodiment about 1 mm to about 0.5 m, and in one embodiment about 2 mm to about 10 cm. The length of the liquid channels 170 may range from about 1 mm to about 1 m, and in one embodiment about 1 cm to about 0.5 m. The separation between each process microchannel 110 and the next adjacent liquid channel 170 may range from about 0.05 mm to about 5 mm, and in one embodiment about 0.2 mm to about 2 mm.

In one embodiment, the process microchannels 110 and liquid channels 170 have rectangular cross sections and are aligned in side by side or stacked planes. This planar configuration provides a number of advantages. In comparison with circular channels, rectangular channels incur less pressure drop while the same shear force is realized for the height or width, or diameter at the same continuous phase mass flux. When the aspect ratio of the rectangular channel approaches 1.0, for example up to about 0.95, its pressure drop is only about 50% of that in circular channel under the same conditions. An array of planar channels can be easily arranged into a compact device for scale-up. Also, in comparison with circular channels, a higher capacity per unit volume of the device can be achieved.

Nevertheless, the process microchannels 110 and the liquid channels 170 may be circular in shape and arranged in a concentric arrangement, with either channel 110 or 170 being in the annular space and the other channel being in the center space. The apertured section 140 may comprise a cylindrical tube. In one embodiment, there may be a large array of interleaved process microchannels 110 and liquid channels 170, alternating between process microchannels 110 and liquid channels 170, where the entire apparatus is in a cylindrical arrangement.

Figure 11:
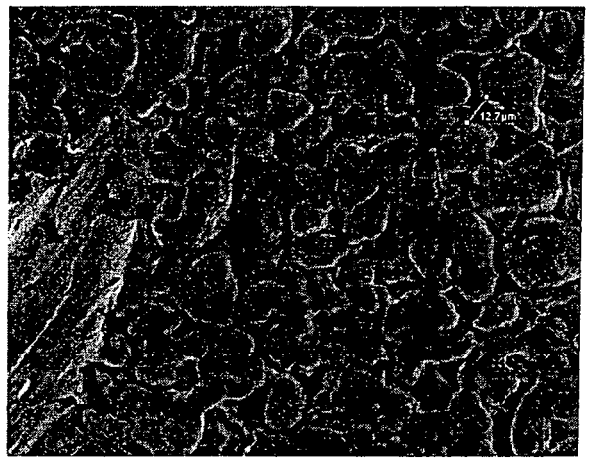
FIG. 11 is an SEM image of a porous stainless steel substrate before being heat treated.
Figure 12:
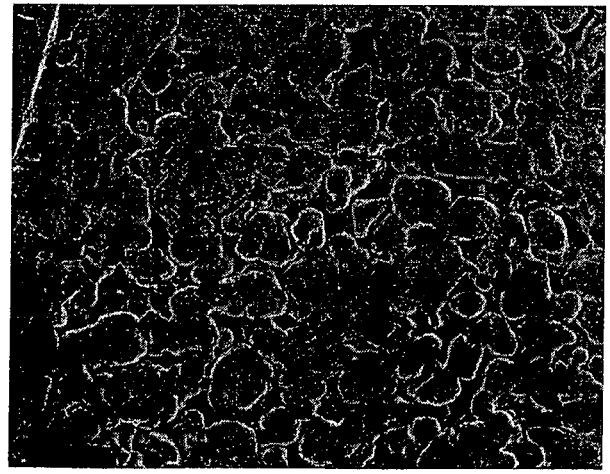
FIG. 12 is an SEM image of the substrate illustrated in FIG. 11 after being heat treated.

The apertured section 140 may comprise a sheet or plate 142 having an array of apertures 144 of sufficient size to enable the second liquid to flow from the liquid channel 170 through the apertures 144 into the process microchannel 110. The apertures 144 may be referred to as pores. The sheet or plate 142 may have a thickness of about 0.01 to about 5 mm, and in one embodiment about 0.05 to about 3 mm, and in one embodiment about 0.1 to about 2 mm. The apertures 144 may have an average diameter of up to about 50 microns, and in one embodiment about 0.01 to about 50 microns, and in one embodiment about 0.05 to about 50 microns, and in one embodiment about 0.1 to about 50 microns. The number of apertures 144 in the sheet or plate 142 may range from about 10 to about $1 \times 10^{10}$ apertures 144 per square centimeter of sheet or plate 142, and in one embodiment about 1 to about $1 \times 10^9$ apertures per square centimeter. The apertures may not be isolated to each other. A portion or all of them may have fluid communications. The ratio of the thickness of the sheet or plate 142 to the length of the apertured section 140 along the flow path of the liquids flowing through the process microchannel 110 may range from about 0.01 to about 1, and in one embodiment about 0.03 to about 1, and in one embodiment about 0.05 to about 1, and in one embodiment about 0.08 to about 1, and in one embodiment about 0.1 to about 1. The sheet or plate 142 may be constructed of any material that provides sufficient strength and dimensional stability to permit the operation of the inventive process. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof. The apertures 144 may be formed using known techniques such as laser drilling, microelectro machining system (MEMS), lithography electrodeposition and molding (LIGA), electrical sparkling or electrochemical etching. The apertures 144 may also be formed using known techniques such as sintering or compressing metallic powder or particles to form tortuous interconnected capillary channels and the techniques of membrane fabrication. The aperatures may be reduced in size from the size provided by any of these methods by the application of coatings over the apertures internal side walls to partially fill the apertures. The aperatures may be reduced in size by heat treating as well as by methods that form an oxide scale on the internal side walls of the apertures. These techniques may be used to partially occlude the aperatures to reduce the size of the openings for flow. FIGS. 11 and 12 show a comparison of SEM surface structures of a stainless steel porous substrate before and after heat treatment at the same magnification and the same location. FIG. 11 shows the surface before heat treating and FIG. 12 shows the surface after heat treating. The surface of the porous material after the heat treatment has a significantly smaller gap and opening size. The average distance between the openings is correspondingly increased.

The apertured section 140 may be made from a metallic or nonmetallic porous material having interconnected tortuous tiny channels or pores of an average pore size of about 0.05 to about 200 microns. These pores may function as apertures for the second liquid to flow through to form droplets in process microchannel 110. The porous material may be made from powder or particulates so that the average inter-pore distance is similar to the average pore size. When very small pore sizes are used, the inter-pore distance will also be very small and the droplets may merge at the surface in the side of process microchannel 110 to form unwanted larger droplets. The porous material may be tailored by oxidization at a high temperature of about 300° C. to about 1000° C. for a duration of about 2 hours to about 20 days, or by coating a thin layer of another material such as alumina by SOL coating or nickel using chemical vapor deposition over the surface and the inside of pores to block the smaller pores, decrease pore size of larger pores, and in turn increase the inter-pore distance. As such, the merger of droplets may be reduced or eliminated and the formation of smaller droplets may be permitted.

During the inventive process, the process microchannels 110 may be heated or cooled using heat exchange channels 190. The heat exchange channels 190 illustrated in FIG. 1 are adapted for heat exchange fluid to flow through the channels in a direction parallel to and co-current with the flow of liquid through the process microchannels 110, as indicated by directional arrows 192. Alternatively, the heat exchange fluid may flow through the heat exchange channels 190 in a direction opposite to the direction indicated in FIG. 1, and thus flow countercurrent to the flow of liquid through the process microchannels 110. Alternatively, the heat exchange channels 190 may be oriented relative to the process microchannels 110 to provide for the flow of heat exchange fluid in a direction that is cross-current relative to the flow of liquid through the process microchannels 110.

The heat exchange channels 190 may be microchannels. Each of the heat exchange channels may have an internal dimension of height or width of up to about 10 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. The other internal dimension may range from about 1 mm to about 1 m, and in one embodiment about 1 mm to about 0.5 m, and in one embodiment about 2 mm to about 10 cm. The length of the heat exchange channels may range from about 1 mm to about 1 m, and in one embodiment about 1 cm to about 0.5 m. The separation between each process microchannel 110 and the next adjacent heat exchange channel 190 may range from about 0.05 mm to about 5 mm, and in one embodiment about 0.2 mm to about 2 mm.

The heat exchange fluid may be any fluid. These include air, steam, liquid water, gaseous nitrogen, liquid nitrogen, other gases including inert gases, carbon monoxide, molten salt, oils such as mineral oil, and heat exchange fluids such as Dowtherm A and Therminol which are available from Dow-Union Carbide.

The heat exchange fluid may comprise the first liquid or second liquid. This can provide process pre-heat or pre-cooling and increase overall thermal efficiency of the process.

In one embodiment, the heat exchange channels 190 comprise process channels wherein an endothermic or exothermic reaction is conducted. Examples of endothermic reactions that may be conducted in the heat exchange channels include steam reforming and dehydrogenation reactions. Examples of exothermic reactions that may be conducted in the heat exchange channels include ammonia synthesis and the conversion of synthesis gas to methanol.

In one embodiment, the heat exchange fluid undergoes a phase change as it flows through the heat exchange channels 190. This phase change provides additional heating or cooling beyond that provided by single phase convective heating or cooling. Examples of such phase changes include the condensation or boiling of oil or water.

The heat exchange channels 190 may be used to heat the first and second liquids, and the emulsion formed in the process microchannel 110 in order to maintain sterile conditions. Unlike batch mixers, the inventive process may be closed to the environment and does it need an inert gas blanket for isolation from the environment. The heat exchange channels 190, which may be adjacent to the process microchannels 110, may provide a short heat transport and diffusion distance; this results in the ability to heat and cool the liquids in the system rapidly with decreased temperature gradients. As a result, emulsions that are not suitable for prolonged heating or would degrade under large temperature gradients may be prepared using the inventive process.

The process microchannels 110, liquid channels 170 and heat exchange channels 190 may be made of any material that provides sufficient strength, dimensional stability and heat transfer characteristics to permit the operation of the inventive process. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof.

The first liquid and the second liquid that are mixed with each other in accordance with the inventive process are immiscible relative to each other. Both liquids may be organic, for example, one liquid may be benzene and the other may be glycerol. One of the liquids may be an ionic liquid (e.g., a salt of 1-butyl-3-methylimidazolium) while the other is an organic liquid. One of the liquids may comprise water, and the other liquid may comprise a hydrophobic organic liquid such as an oil. The emulsion made by the inventive process may be referred to as a water-in-oil emulsion or an oil-in-water emulsion. Throughout the specification and in the claims the term "oil" is sometimes used to refer to an organic phase of an emulsion although the organic material may or may not technically be an oil. In one embodiment, the emulsion made by the inventive process is characterized by a dispersed phase, the dispersed phase being comprised of droplets having a mean diameter of up to about 50 microns, and in one embodiment about 0.01 to about 50 microns, and in one embodiment about 0.01 to about 25 microns, and in one embodiment about 0.01 to about 10 microns, and in one embodiment about 0.01 to about 5 microns, and in one embodiment about 0.01 to about 2 microns, and in one embodiment about 0.01 to about 1 micron, and in one embodiment about 0.01 to about 0.5 micron, and in one embodiment about 0.01 to about 0.2 micron, and in one embodiment about 0.01 to about 0.1 micron, and in one embodiment about 0.01 to about 0.08 micron, and in one embodiment about 0.01 to about 0.05 micron, and in one embodiment about 0.01 to about 0.03 micron. In one embodiment, the dispersed phase comprises water. In one embodiment, the dispersed phase comprises an organic or oil phase.

An advantage of the inventive process is that at least in one embodiment the droplets are characterized by having a relatively narrow distribution of droplet sizes. In one embodiment, the droplets sizes in the dispersed phase may be plotted and as such would form a normal distribution curve. The mean diameter of the droplets may range from about 0.01 to about 50 microns, as indicated above, and the standard deviation for the droplet size may range from about 0.001 to about 10 microns, and in one embodiment about 0.001 to about 5 microns, and in one embodiment about 0.001 to about 2 microns, and in one embodiment about 0.001 to about 1 micron, and in one embodiment about 0.001 to about 0.5 micron, and in one embodiment about 0.001 to about 0.1 micron, and in one embodiment about 0.001 to about 0.05 micron.

In one embodiment, the emulsion produced by the inventive process may be terminally filtered or filtered in-line. The use of such filtering is particularly suitable for producing emulsions such as pharmaceutical compositions where sterilization issues are significant. With such filtering relatively large particles of contaminants (e.g., biological materials) may be removed. In one embodiment, the inventive process includes providing for the filtering of the product emulsion in-line in a continuous closed (i.e., antiseptic) process.

Figure 9:
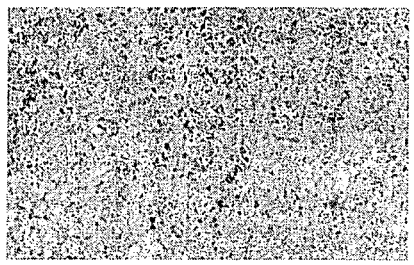
FIG. 9 is a microscopic image of an emulsion made by the inventive process.
Figure 10:
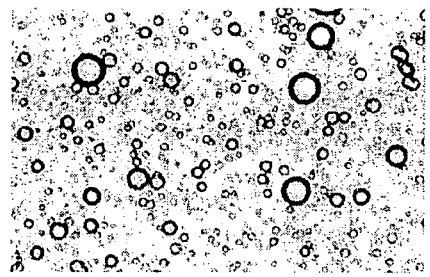
FIG. 10 is a microscopic image of an emulsion made by a batch emulsification process.

A comparison of an emulsion made using the inventive process having a narrow distribution of droplet sizes to an emulsion made using a conventional batch emulsification process may be provided with reference to FIGS. 9 and 10. FIG. 9 is a microscopic image of an emulsion made by the inventive process while FIG. 10 shows an emulsion made by a conventional process. The droplets in FIG. 11 have a wide size distribution and larger droplet sizes. The droplets in FIG. 10 have a relatively narrow size distribution and smaller droplet sizes. The benefits of narrow droplet size distribution include, for example, uniform spread of active ingredients on an applied surface such as skin, and exclusions of unwanted small droplet penetration into small scale surface structures that may occur using an emulsion having a wide distribution. Another advantage relates to reducing the use of surfactants, as the necessary concentration of surfactant to maintain a stable emulsion usually increases as the smallest droplet size decreases within a range, for example, from about 2 to about 20 microns. A narrow droplet size distribution eliminates producing unnecessary smaller droplets and in turn the unnecessary surfactant amount requirement. A wide droplet size distribution often leads to using excess surfactant. On the other hand, when the droplet size is sufficiently small, for example, smaller than about 0.1 micron, a narrow droplet size distribution from the inventive process may ensure a significant elimination of surfactant addition, as these small droplets may stabilize.

The organic or oil phase liquid may comprise a natural oil, synthetic oil or mixture thereof. The natural oils include animal oils and vegetable oils (e.g., castor oil, lard oil) as well as mineral oils such as liquid petroleum oils and solvent treated or acid-treated mineral oils of the paraffinic, naphthenic or mixed paraffinic-naphthenic types. The natural oils include oils derived from coal or shale are also useful. Synthetic oils include hydrocarbon oils such as polymerized and interpolymerized olefins (e.g., polybutylenes, polypropylenes, propylene isobutylene copolymers, etc.); poly(1-hexenes), poly-(1-octenes), poly(1-decenes), etc. and mixtures thereof; alkylbenzenes (e.g., dodecylbenzenes, tetradecylbenzenes, dinonylbenzenes, di-(2-ethylhexyl)benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like. Alkylene oxide polymers and interpolymers and derivatives thereof where the terminal hydroxyl groups have been modified by esterification, etherification, etc., constitute a class of known synthetic oils that may be used. Esters of dicarboxylic acids (e.g., phthalic acid) with a variety of alcohols (e.g., butyl alcohol, hexyl alcohol) may be used. The oil may be a poly-alpha-olefin or a Fischer-Tropsch synthesized hydrocarbon. The oil may be a saponifiable oil from the family of triglycerides, for example, soybean oil, sesame seed oil, cottonseed oil, safflower oil, and the like.

The organic liquid or oil may be present in the emulsion made by the inventive process at a concentration of about 0.1 to about 99.9% by weight, and in one embodiment about 1 to about 99% by weight, and in one embodiment about 5 to about 95% by weight.

The water used in the inventive process may be taken from any convenient source. The water may be deionized or purified using osmosis or distillation. The water may be present in the emulsion made by the inventive process at a concentration of about 99.9 to about 0.1% by weight, and in one embodiment about 99 to about 1% by weight, and in one embodiment about 95 to about 5% by weight.

Although surfactants are not required for various embodiments of the invention, it is possible to use one or more surfactants in forming the emulsions prepared by the inventive process. The surfactants may comprise ionic or nonionic compound having a hydrophilic lipophilic balance (HLB) in the range of about 0.01 to about 0.99, and in one embodiment about 0.1 to about 0.9. The ionic compounds may be cationic or amphoteric compounds. Examples are disclosed in *McCutcheons Surfactants and Detergents,* 1998, North American & International Edition. Pages 1-235 of the North American Edition and pages 1-199 of the International Edition are incorporated herein by reference for their disclosure of such emulsifiers. The surfactants that may be used include alkanolamines, alkylarylsulfonates, amine oxides, poly(oxyalkylene) compounds, including block copolymers comprising alkylene oxide repeat units, carboxylated alcohol ethoxylates, ethoxylated alcohols, ethoxylated alkyl phenols, ethoxylated amines and amides, ethoxylated fatty acids, ethoxylated fatty esters and oils, fatty esters, fatty acid amides, glycerol esters, glycol esters, sorbitan esters, imidazoline derivatives, lecithin and derivatives, lignin and derivatives, monoglycerides and derivatives, olefin sulfonates, phosphate esters and derivatives, propoxylated and ethoxylated fatty acids or alcohols or alkyl phenols, sorbitan derivatives, sucrose esters and derivatives, sulfates or alcohols or ethoxylated alcohols or fatty esters, sulfonates of dodecyl and tridecyl benzenes or condensed naphthalenes or petroleum, sulfosuccinates and derivatives, and tridecyl and dodecyl benzene sulfonic acids. The surfactant may be a pharmaceutically acceptable material such as lecithin. The concentration of these surfactants in the emulsions made by the inventive process may range up to about 20% by weight of the emulsion, and in one embodiment about 0.01 to about 5% by weight, and in one embodiment about 0.01 to about 2% by weight.

Figure 13:
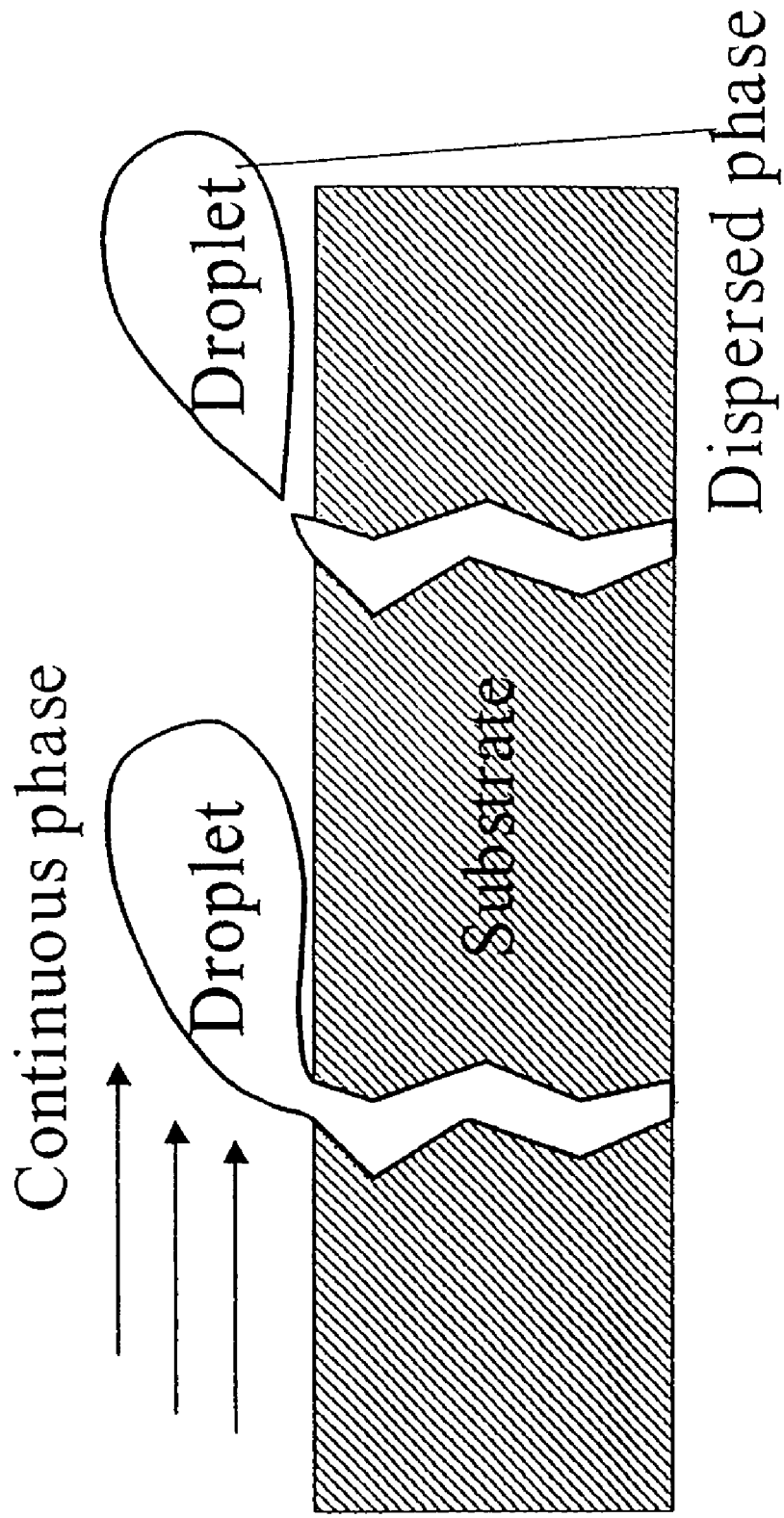
FIG. 13 is a schematic illustration showing the formation of a droplet during the operation of the inventive process.

The flow rate of the first liquid flowing through the process microchannel 110 may range from about 0.001 to about 500 liters per minute (lpm), and in one embodiment 0.001 to about 250 lpm, and in one embodiment about 0.001 to about 100 lpm, and in one embodiment about 0.001 to about 50 lpm, and in one embodiment about 0.001 to about 25 lpm, and in one embodiment about 0.01 to about 10 lpm. The velocity of the first liquid flowing through the process microchannel 110 may range from about 0.01 to about 100 meters per second (m/s), and in one embodiment about 0.01 to about 75 m/s, and in one embodiment about 0.01 to about 50 m/s, and in one embodiment about 0.01 to about 30 m/s, and in one embodiment about 0.02 to about 20 m/s. The Reynolds Number for the first liquid flowing through the process microchannel 110 may range from about 0.0001 to about 100000, and in one embodiment about 0.001 to about 10000. The temperature of the first liquid entering the process microchannel 110 may range from about 0° C. to about 200° C., and in one embodiment about 20° C. to about 100° C. The first liquid entering the process microchannel 110 may be at a pressure of about 0.01 to about 100 atmospheres, and in one embodiment about 1 to about 10 atmospheres. In the inventive process, a relatively high pressure drop across the apertured section 140 or a correspondingly high dispersion phase liquid flow rate through the liquid channel 170 is not a necessary requirement to achieve the desired disbursement of the dispersed phase as is often the case in, for example, high pressure homogenizers. A low flow rate or low pressure drop leads to a smaller droplet size with the inventive process, as lower inertia of the dispersion phase flow through the aperture reduces droplet growth before droplet breakup. This is shown schematically in FIG. 13.

The flow rate of the second liquid flowing through the liquid channel 170 may range from about 0.05 to about 5000 milliliters per second (ml/s), and in one embodiment about 0.1 to about 500 ml/s. The velocity of the second liquid flowing through the liquid channel 170 may range from about 0.0001 to about 0.1 m/s, and in one embodiment about 0.0001 m/s to about 0.05 m/s. The Reynolds Number for the second liquid flowing through the liquid channel 170 may range from about 0.0000001 to about 1000, and in one embodiment about 0.0001 to about 100. The temperature of the second liquid entering the liquid channel 170 may range from about −20° C. to about 250° C., and in one embodiment about 20° C. to about 100° C. The second liquid entering the liquid channel 170 may be at a pressure of about 1 to about 200 atmospheres, and in one embodiment about 1 to about 100 atmospheres. The pressure drop for the second liquid flowing through the apertures 144 may range from about 0.05 to about 200 atmospheres, and in one embodiment about 1 to about 150 atmospheres.

The emulsion exiting the process microchannel 110 may be at a temperature of about −20° C. to about 200° C., and in one embodiment about 0° C. to about 100° C.

The heat exchange fluid entering the heat exchange channel 190 may have a temperature of about −50° C. to about 300° C., and in one embodiment about −10 to about 200° C., and in one embodiment about 0° C. to about 100° C. The heat exchange fluid exiting the heat exchange channel 190 may have a temperature in the range of about 0° C. to about 200° C., and in one embodiment about 10° C. to about 200° C. The pressure drop for the heat exchange fluid as it flows through the heat exchange channels may range from about 0.01 to about 20 atmospheres, and in one embodiment from about 0.1 to about 20 atmospheres. The flow of the heat exchange fluid through the heat exchange channels may be laminar or in transition, and in one embodiment it is laminar. The Reynolds Number for the flow of heat exchange fluid flowing through the heat exchange channels may be up to about 100000, and in one embodiment up to about 10000, and in one embodiment in the range of about 20 to about 10000, and in one embodiment about 100 to about 5000.

The process liquids may be preheated in the emulsion forming unit or prior to entering the emulsion forming unit using any type of heat exchange device, including a microchannel heat exchanger or heat pipe. The emulsion product produced in the emulsion forming unit may be cooled in the emulsion forming unit or upon exiting the emulsion forming unit using any type of heat exchange device, including a microchannel heat exchanger. In one embodiment, a rapid cooling of the emulsion may be used to stabilize the emulsion or lock it in. In one embodiment, the emulsion may be cooled to room temperature in up to about 10 minutes, and in one embodiment up to about 5 minutes, and in one embodiment up to about 1 minute, and in one embodiment up to about 30 seconds, and in one embodiment up to about 10 seconds.

Figure 2:
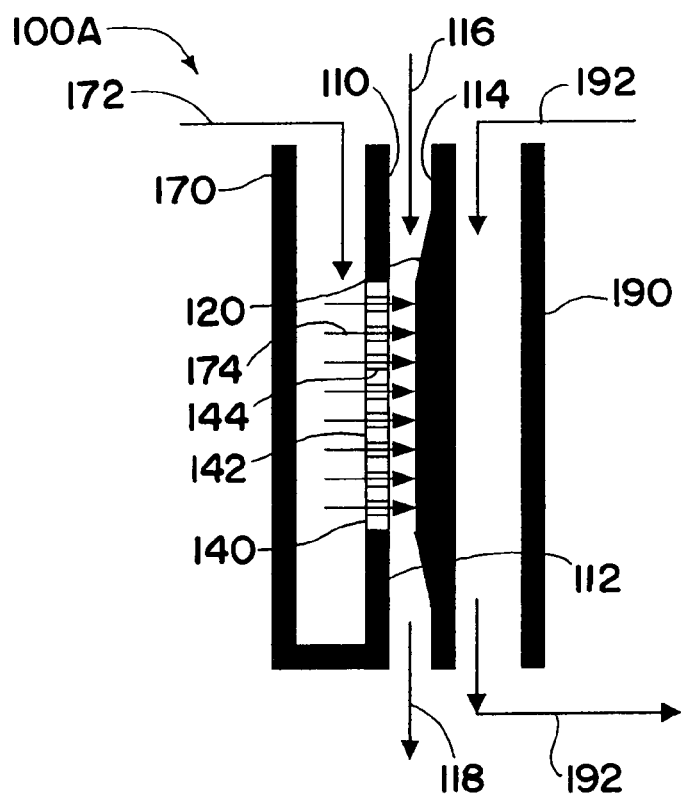
FIG. 2 is a flow sheet illustrating an alternate embodiment of the inventive process.

The process illustrated in FIG. 2 is identical to the process illustrated in FIG. 1 with the exception that the sidewall 114 of process microchannel 110 includes tapered section 120 which is aligned opposite apertured section 140. Tapered section 120 reduces the width or height of the process microchannel 110 in the area adjacent to apertured section 140. The width or height may be about 0.001 to about 5 mm, and in one embodiment about 0.01 to about 2 mm. The presence of tapered section 120 provides for an increase in the velocity of the liquid flowing through process microchannel 110 in the region adjacent to tapered section 120. The increased velocity of the liquid flow in this section results in an increased shear force acting on the outcoming dispersion phase liquid and a reduced pressure exerted by the flowing liquid in the direction toward the apertured section 140. This facilitates the flow of the second liquid through the apertures 144 into the process microchannel 110. The velocity of liquid flowing past the tapered section may range from about 0.005 to about 20 m/s, and in one embodiment about 0.01 to about 20 m/s.

Figure 3:
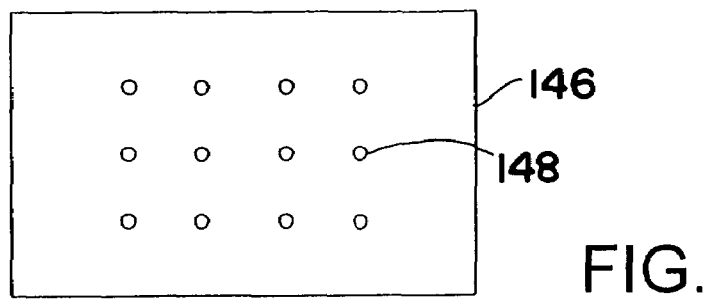
FIG. 3 is a plan view of an apertured sheet which is useful in making the apertured section of the process microchannel used with the inventive process.
Figure 4:
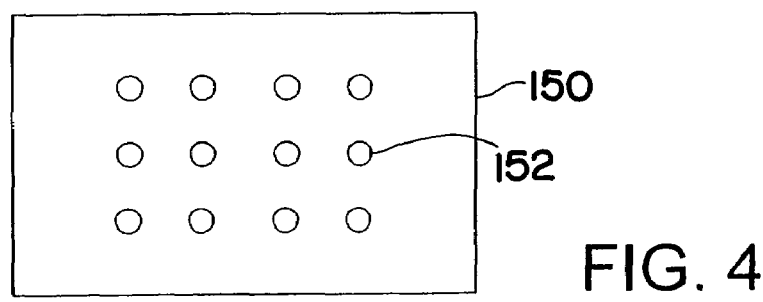
FIG. 4 is a plan view of an apertured sheet or plate which is useful in making the apertured section of the process microchannel used with the inventive process.
Figure 5:
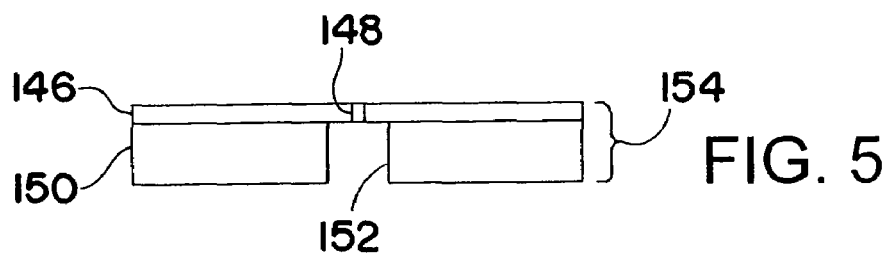
FIG. 5 is an illustration of a relatively thin apertured sheet overlying a relatively thick apertured sheet or plate which is useful in making the apertured section of the process microchannel used with the inventive process.

Referring to FIGS. 3-5, the apertured section 140 may, in one embodiment, be constructed of a relatively thin sheet 146 containing an array of relatively small apertures 148, and a relatively thick sheet or plate 150 containing an array of relatively large apertures 152 which are aligned with apertures 148. The relatively thin sheet 146 overlies and is bonded to the relatively thick sheet 150, the relatively thin sheet 146 facing the interior of process microchannel 110 and the relatively thick sheet 150 facing the interior of liquid channel 170. The relatively thin sheet 146 may be bonded to the relatively thick sheet 150 using any suitable procedure (e.g., diffusion bonding) to provide a composite construction 154 with enhanced mechanical strength. The relatively thin sheet 146 may have a thickness of about 0.001 to about 0.5 mm, and in one embodiment about 0.05 to about 0.2 mm. The relatively small apertures 148 may have any shape, for example, circular, triangular or rectangular. The relatively small apertures 148 may have an average diameter of about 0.05 to about 50 microns, and in one embodiment about 0.05 to about 20 microns. The relatively thick sheet or plate 150 may have a thickness of about 0.1 to about 5 mm, and in one embodiment about 0.1 to about 2 mm. The relatively large apertures 152 may have any shape, for example, circular, triangular or rectangular. The relatively large apertures 152 may have an average diameter of about 10 to about 4000 microns, and in one embodiment about 10 to about 2000 microns, and in one embodiment about 10 to about 1000 micron. The array of apertures 148 in sheet 146 and the array of apertures 152 in sheet or plate 150 may each comprise about 2 to about 10000 apertures per square centimeter, and in one embodiment about 2 to about 1000 apertures per square centimeter. The sheet 146 and the sheet or plate 150 may be constructed of any of the materials described above as being useful for constructing the sheet or plate 142. The apertures 148 and 152 may be coaxially aligned such that liquid flowing from liquid channel 170 to process microchannel 110 flows initially through apertures 152 then through apertures 148. The relatively short passageway for the liquid to flow through the relatively small apertures 148 enables the liquid to flow through the apertures 148 with a relatively low pressure drop as compared to the pressure drop that would occur if the passageway in the apertures had a length equal to the combined length of apertures 146 and 152.

Figure 6:
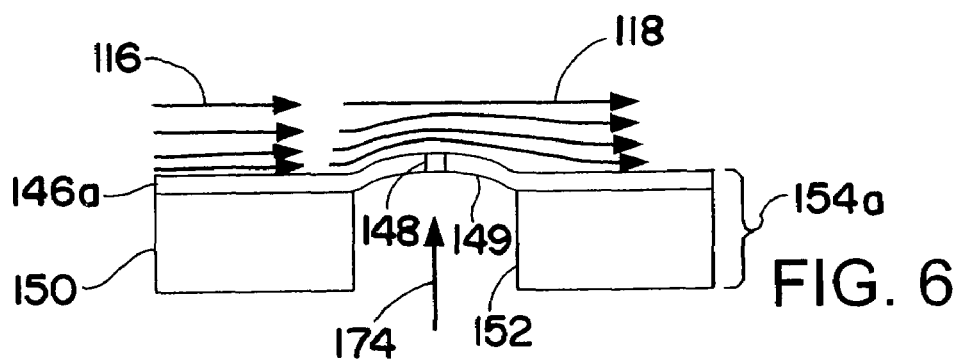
FIG. 6 is illustrative of a relatively thin apertured sheet overlying a relatively thick apertured sheet or plate which is useful in making the apertured section of the process microchannel used with the inventive process.

In the embodiment illustrated in FIG. 6, the composite construction 154a has the same design as illustrated in FIG. 5 with the exception that convex portion 149 of the relatively thin sheet 146 covering the aperture 152 is provided. Convex portion 149 provides increased local shear force in the process microchannel 110. The directional arrows 116 and 118 in FIG. 6 showing the flow of liquid in the process microchannel 110 adjacent to the aperture 148. The higher shear force leads to a smaller droplet size for the second liquid.

Figure 7:
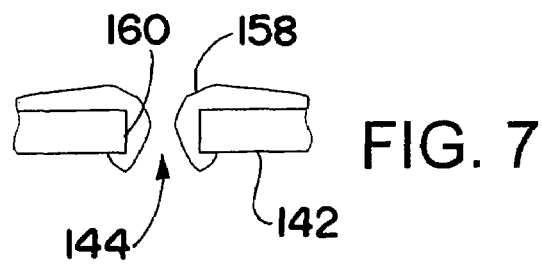
FIG. 7 is illustrative of an alternated embodiment of an aperture that may be used in the apertured section of the process microchannel used with the inventive process, the aperture having a coating partially filling it and overlying its sidewalls.

In the embodiment illustrated in FIG. 7, a surface coating 158 is deposited on the surface of sheet or plate 142 and on the internal sidewalls 160 of aperture 144. This coating provides a facilitated way of reducing the diameter of the apertures 144. The coating material used to form coating 158 may be alumina, nickel, gold, or a polymeric material (e.g., Teflon). The coating 158 may be applied to the sheet or plate 142 using known techniques including chemical vapor deposition, metal sputtering, metal plating, sintering, sol coating, and the like. The diameter of the apertures 144 may be controlled by controlling the thickness of the coating 158.

Figure 14:
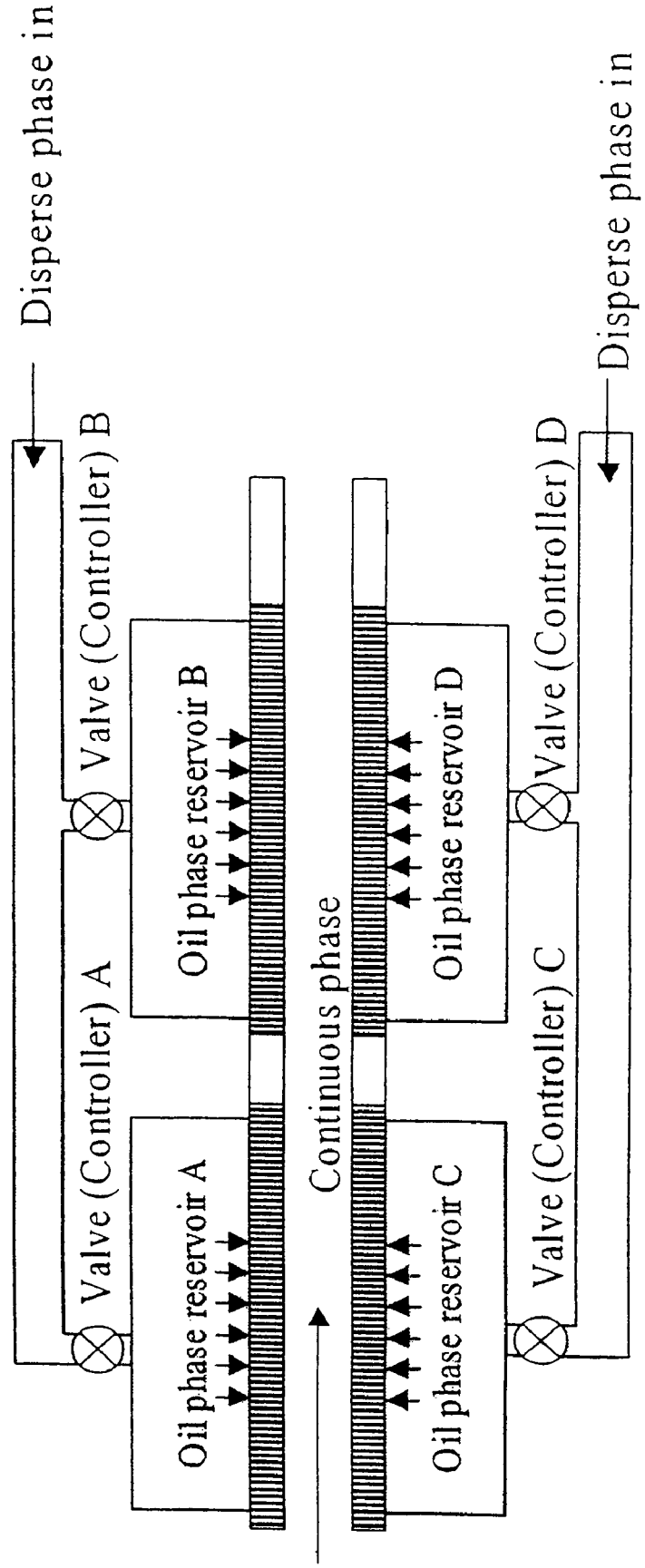
FIG. 14 is a flow sheet illustrating an alternate embodiment of the inventive process wherein multiple disperse phase reservoirs are used.

In one embodiment, multiple disperse phase liquid reservoirs or chambers may be built around the continuous phase channels, as illustrated in FIG. 14. The individual reservoirs or chambers may be separated and have their own inlet control mechanism such as valves. In this configuration the volumetric ratio of the two phases (packing density) may be controlled and changed according to different formulations of the desired product emulsions without changing other components such as aperture or pore size of the apertured section or individual flow rates of the continuous phase or the disperse phase. This is useful for an "one pass process" (i.e., without recirculation). For example, if all reservoirs or chambers A, B, C and D have the same oil flow rates and pore size, the emulsion packing density by closing valves A and B will be 50% of that by opening all valves. It is noted that various modifications of this concept are possible, for example more than two oil reservoirs or chambers can be configured on each side of the continuous phase channel. Multiple continuous phase channels may be parallel interleaved (sandwiched) to form an array of process channels. In FIG. 14, the disperse phase is identified as an oil phase, however, those skilled in the art will recognize that the dispersed phase may be any liquid that is immiscible with the continuous phase liquid.

The emulsions made by the inventive process have numerous applications. These include personal care products wherein reduced concentrations of emulsifiers or surfactants are desirable (e.g., waterproof sun screen, waterproof hand creams or lotions). These also include paints such as water-resistant latex paints with strong weatherability characteristics, adhesives, glues, caulks, waterproof sealants, and the like. As a result of the inclusion of an aqueous phase in these compositions, the problem of volatile organic compounds in these products is reduced. The inventive process may be used in various food processing applications, particularly continuous processing operations. The inventive process may be used in the production of agricultural chemicals where the use of a dispersed phase with a narrow distribution of droplet sizes is advantageous for spreading the chemicals on leafs, and providing enhanced waterproofing with smaller concentrations of chemicals. The inventive process may be used for the production of emulsified lubricants and fuels; these may include on-board fuel emulsification systems including those used to start up on-board fuel processor or fuel cell systems. The inventive process may be employed in emulsion polymerization processes. For example, it may be possible to solublize monomers in a surfactant with a catalyst. Emulsions prepared in accordance with the inventive process provide the advantage of enabling the supplier to provide the emulsion in concentrate form, thus enabling the end user to add additional ingredients, such as water or oil.

The inventive process may be used in the manufacture of pharmaceuticals wherein the provision of a dispersed oil phase with a narrow distribution of droplet sizes is advantageous. These may include oral or injectable compositions as well as dermatological creams, lotions and opthalmics. The droplet size and distribution achieved with the inventive process may increase the efficacy of the drug and provide for reduced levels of use of the drug for required treatments. This also provides the advantage of avoiding or limiting the use of non-aqueous solvent components which tend to solubilize organic substances used in packaging materials. The droplet size for the dispersed oil phase for these applications may be up to about 0.5 micron, in order to avoid being eliminated by the spleen or liver, and in one embodiment about 0.01 to about 0.2 micron, and in one embodiment 0.01 to about 0.1 micron. The emulsions produced by the inventive process may function as emulsion vehicles for insoluble or poorly soluble drugs (e.g., ibuprofen, diazepam, griseofulvin, cyclosporin, cortisone, proleukin, etoposide, paclitaxel, cytotoxin, vitamin E, alpha-tocopherol, and the like). Many of the pharmaceutical compounds or drugs, oils and surfactants disclosed in U.S. Patent Application Publication No. 2003/0027858A1 may be used in making pharmaceutical compositions using the inventive process; this patent publication is incorporated herein by reference. An advantage of using the inventive process relates to the fact that many of the problems associated with using conventional high-shear mixing equipment for attempting to achieve small droplets with a narrow droplet size distribution while maintaining a sterile environment are avoided.

EXAMPLE 1

Figure 15:
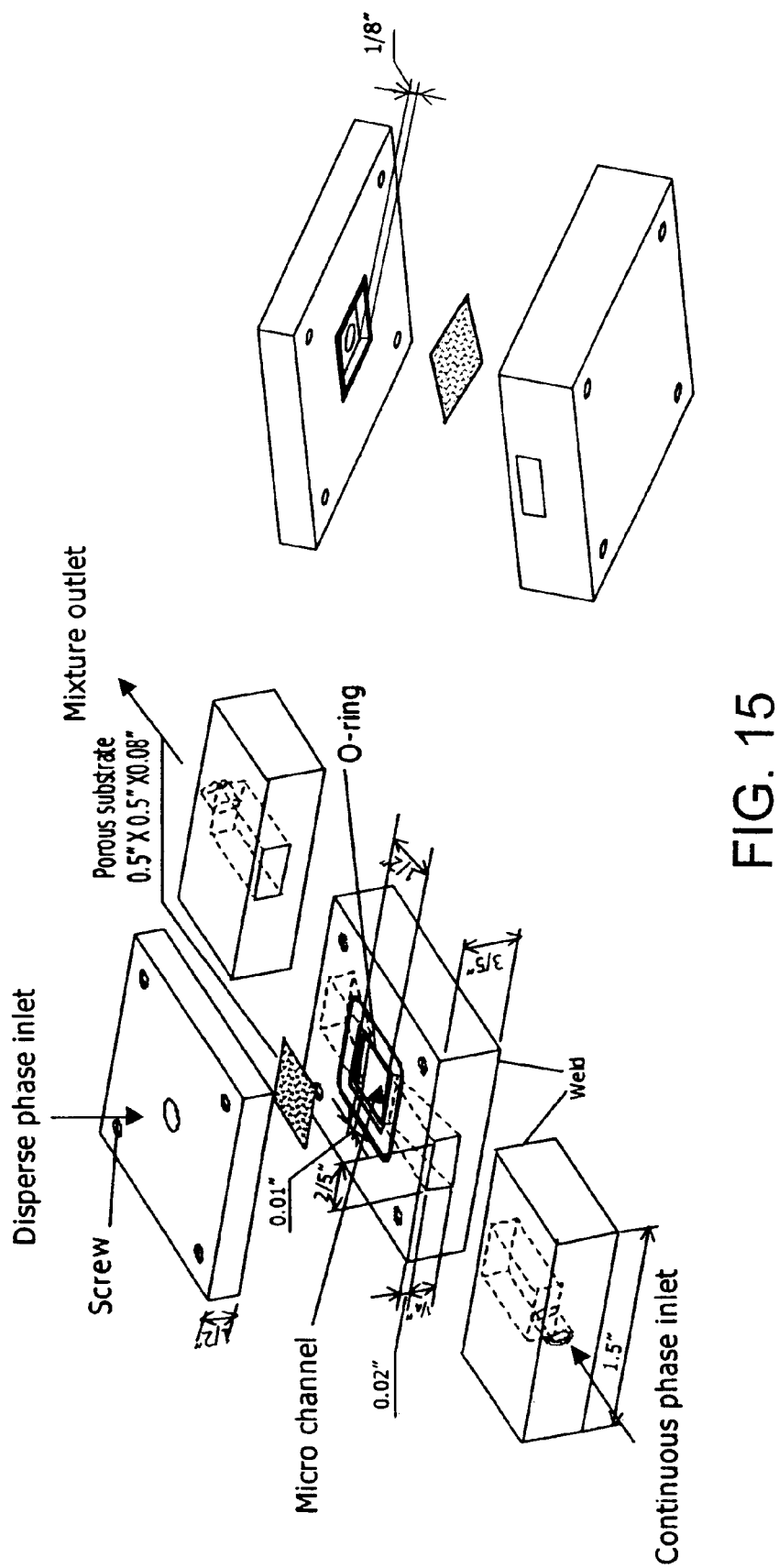
FIG. 15 is a schematic illustration of the microchannel device used in Example 1.

The microchannel device illustrated in FIG. 15 is made from stainless steel and used to form an oil-in-water emulsion. The device includes a base part for continuous phase flow, a top part for delivering a discontinuous oil phase, a porous substrate, a header, a footer, and tubing and piping to provide for the flow of liquids to the microchannel device.

The base part, which has an overall size of $\frac{3}{5} \times 1.5 \times 1.5$ inches, has an open microchannel having the dimensions of 0.02×0.5×0.5 inch, and sloping inlet and outlet flow passageways (0.5 inch long, 0.5 inch wide, slopping angle 27°) that are connected via welding with the header and footer for the continuous phase liquid. The edge of the open microchannel has a lip (step) with a width of 0.02 inch for mounting the porous substrate via rubber gasket of thickness 0.005 inch for sealing. With the mounting of the porous substrate (0.5×0.5× 0.04 inch), a microchannel is formed for providing high velocity flow of a continuous phase and generating micro-scale droplets as a dispersed phase in the continuous phase.

The top part comprises a built-in oil chamber (see right-side figure in FIG. 15) connected to an oil pipe line (not shown in the drawing). The header and footer (the parts with slope and connected spaces) are designed for flow area transition from ordinary tubes to the microchannel with a small gap (less than 1 mm), while the overall pressure drop is maintained at a reasonable value depending upon the pump and heating capacity.

Figure 16:
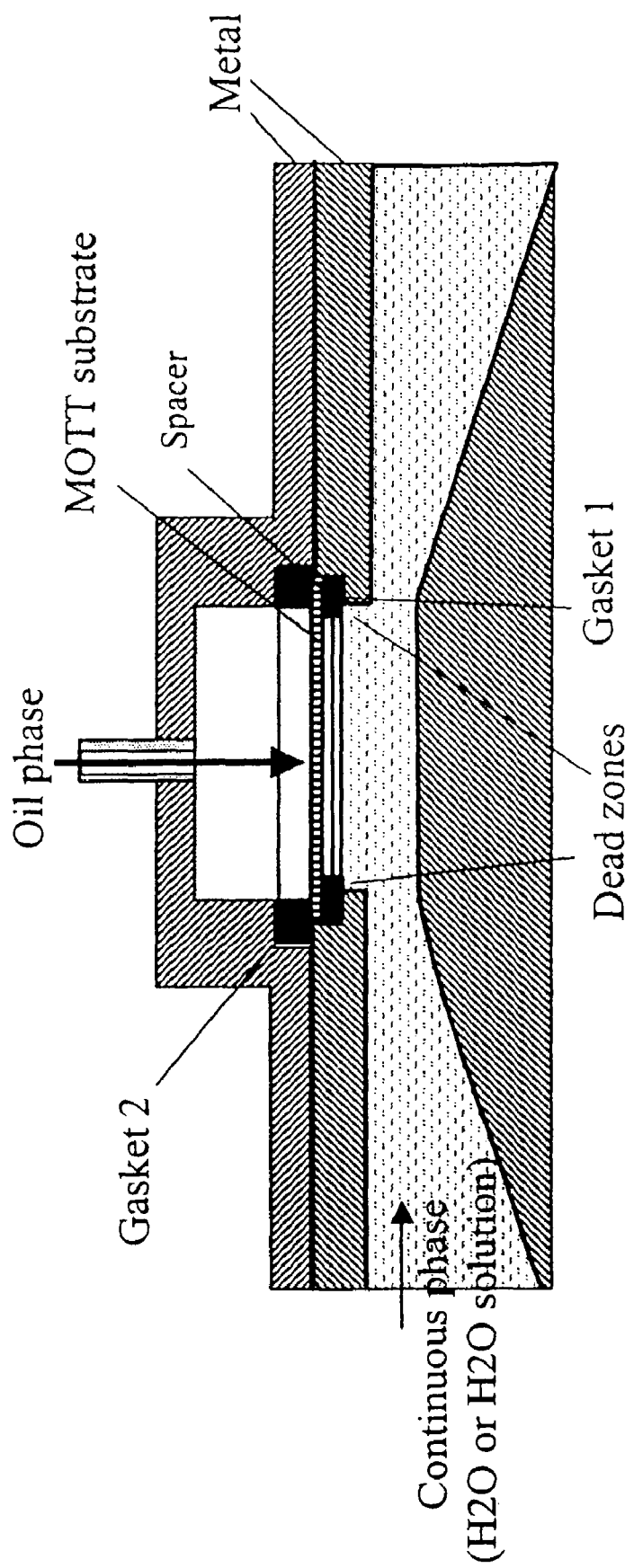
FIG. 16 is another schematic illustration of the microchannel device used in Example 1.

A schematic of the basic structure is illustrated in FIG. 16. The porous substrate is a heat treated porous substrate supplied by MOTT Metallurgical Corp. of Farmington, Conn. The porous substrate is made from stainless steel 316. The average diameter of each pore is 0.5 micron. The porous substrate separates the disperse phase liquid chamber from the continuous phase liquid channel. A pressure difference (10 to 20 psia) during the emulsification operation drives the disperse phase liquid through the porous substrate into the continuous liquid channel which results in the formation of droplets in the continuous phase.

Figure 17:
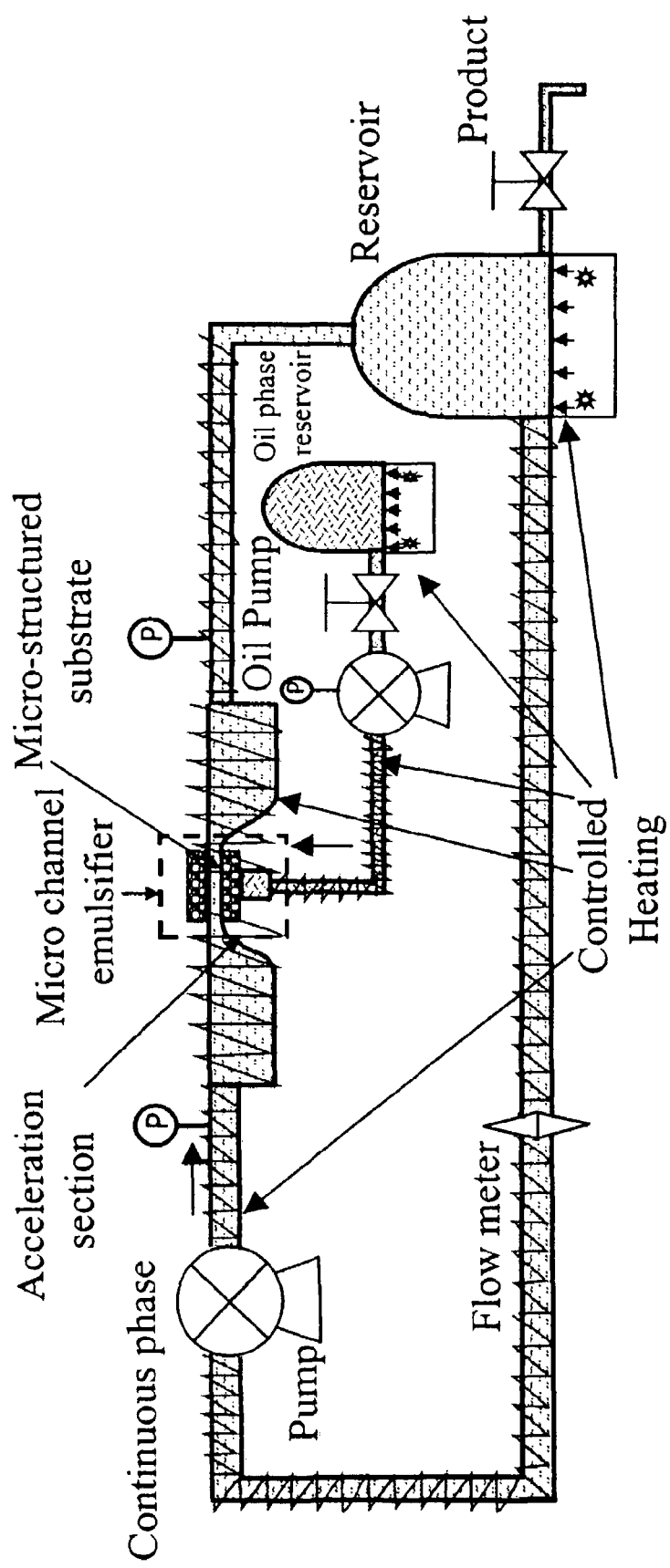
FIG. 17 is a flow sheet illustrating the emulsification system used in Example 1.

The emulsification system is illustrated in FIG. 17. This system includes an oil pump (FMI "Q" pump, Model QG6 from FluidMetering, Inc, Syosset, N.Y.), a water pump with a flow rate dial (Micropump Model GJ-N25, JF18A from Cole Parmer, Vernon Hills, Ill.), a heated oil reservoir, a continuous phase liquid reservoir, and metallic tubings (¼") connecting the pumps and the microchannel emulsifier. An extra rotor flow meter (Cole Parmer) is installed to record the actual flow rate and for later calibration. By installing heating tapes around most of the metallic tubing, exposed components as well as the microchannel device and by feed-back controlling the heating power via TC signals from multiple key locations, all components and the liquids in the system are maintained at a temperature that is higher than the ambient. The components to be heated up and controlled include the microchannel emulsifier, oil pump and reservoir, and water reservoir. The reservoirs have inside volume scales.

Before being used for emulsification, the porous substrate is cleaned and heat-treated. The following cleaning procedure is used:
1. Sonicate in hexane for 5 min. If the porous substrate is pre-exposed to oil, repeat hexane sonication once with fresh hexane.
2. Air dry at room temperature over night, or at 80° C. for 10-20 minutes in a drying oven.
3. Sonicate the porous substrate in 20% nitric acid for 20 minutes.
4. Sonicate the porous substrate in fresh deionized water for 5 minutes.
5. Repeat step #4 at least three times to achieve pH reading of the water of over 5.
6. Sonicate the porous substrate in acetone or isopropanol for 3 minutes.
7. Air dry at room temperature overnight, or at 80° C. for 10-20 minutes in a drying oven.

The porous substrate is then heat treated in a heat treatment vessel using the following procedure:
1. Evacuate and refill with nitrogen three times.
2. Heat in the presence of hydrogen and water to 650° C. at a rate of 3.5° C. per minute.
3. Maintain temperature at 650° C. for 30 minutes with nitrogen flow.
4. Maintain temperature at 650° C. in air for 100 hours.
5. Cool in air to room temperature at a rate of 3.5° C. per minute.

Figure 8:
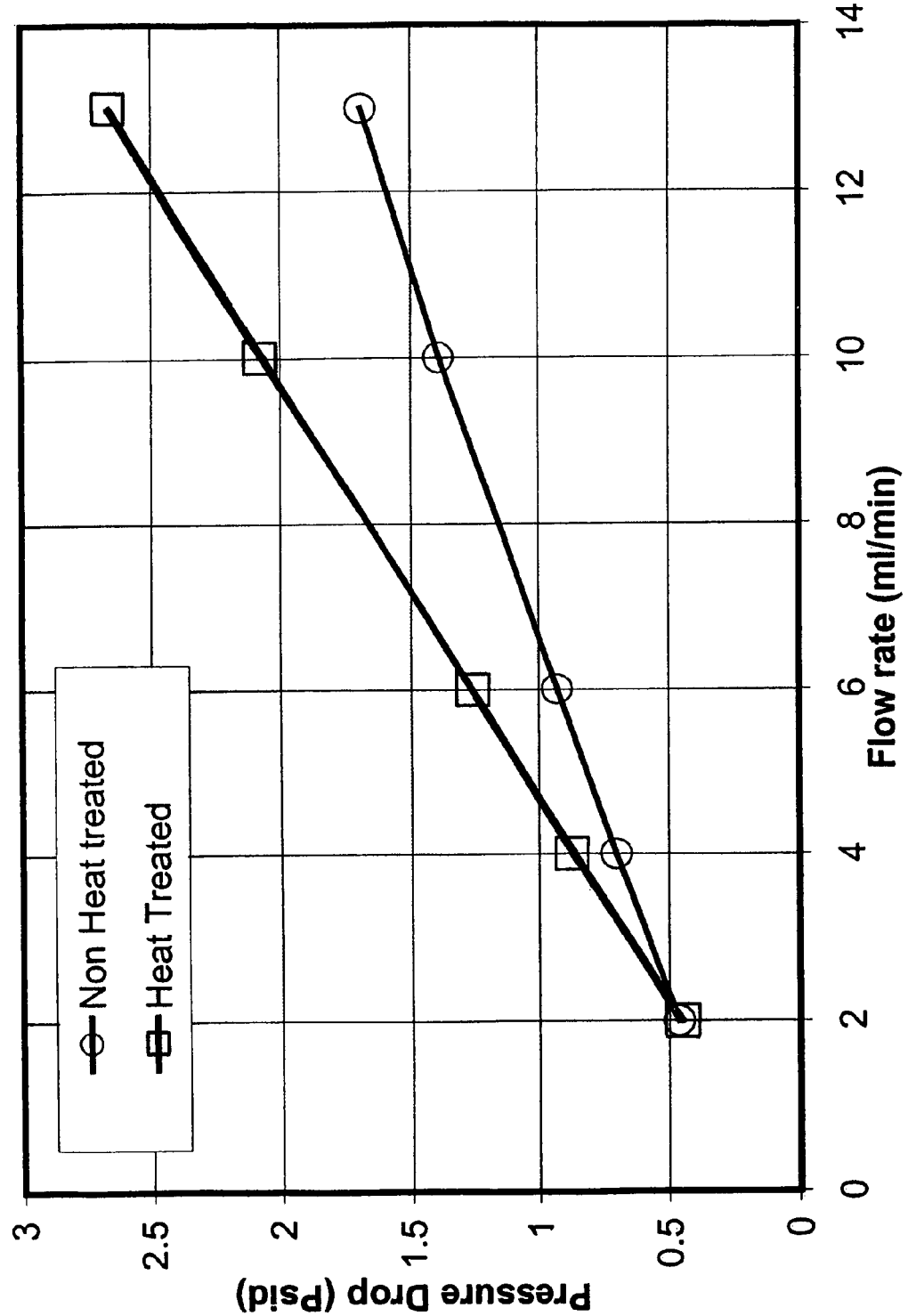
FIG. 8 is a plot of pressure drop versus flow rate for the porous substrates tested in Example 1.

One of the methods to characterize the heat treatment effect on the pore size and number is to conduct permeability tests using water. Using the same flow rate, water is pumped through the heat-treated porous substrate and through an untreated porous substrate. Different pressure drop curves are obtained as shown in FIG. 8. The heat-treated substrate has a higher pressure drop than that of untreated substrate. In this example, the average pore size decreases from 0.5 to 0.44 micron while the intra-pore distance increases from 0.5 to 0.6 micron.

A moisturizing lotion having the formulation indicated below is prepared using the microchannel device.

|  | Parts by Wt. |
|---|---|
| First Liquid (Continuous Aqueous) | |
| Water | 82.90 |
| CARBOPOL 934 (a product supplied by BF Goodrich/Harris and Ford identified as a resin) | 0.20 |
| Na2 EDTA (a product supplied by Dow Chemical Company) | 0.05 |
| Glycerine USP (a product supplied by Humco) | 4.00 |

-continued

|  | Parts by Wt. |
|---|---|
| Second Liquid (Discontinuous Oil) | |
| Stearic Acid | 2.00 |
| Cetyl Alcohol | 0.50 |
| Glyceryl Monostearate | 0.20 |
| Ethylene Glycol Monostearate | 0.30 |
| Propylparaben | 0.10 |
| Methylparaben | 0.20 |
| Mineral Oil | 7.00 |
| SILICONE FLUID DC200 (a product supplied by Dow Corning identified as a silicone fluid) | 1.00 |
| TWEEN 20 (a product supplied by Uniqema Americas (ICI) identified as a surfactant) | 0.50 |
| Triethanolamine | 0.90 |

The following process steps are used:
1. All ingredients in the Second Liquid are mixed in a beaker and heated to 75° C. The triethanolamine is added last. The Second Liquid is then maintained at 75° C. in the oil phase reservoir.
2. Prepare the First Liquid by dispersing the CARBOPOL 934 in the water and heating to 75° C. The remaining ingredients for the First Liquid are then added. The First Liquid is maintained at 75° C. in the reservoir that is connected to the continuous phase liquid pump.
3. The heating powers of the system for all components are adjusted and stabilized at 75±10° C.
4. The continuous phase liquid pump is activated and set for a flow rate of 2.5 l/min.
5. The oil pump is activated and set for a flow rate of 2.5 ml/min. The pressure drop across the porous substrate is maintained at 10-20 psia.
6. The First Liquid is recirculated until the desired amount of the Second Liquid is mixed with the First Liquid.
7. The product emulsion is cooled to a temperature below 38° C. by placing the reservoir in a cold water/ice bath or by turning on a cooling coil built in the reservoir.

Figure 18:
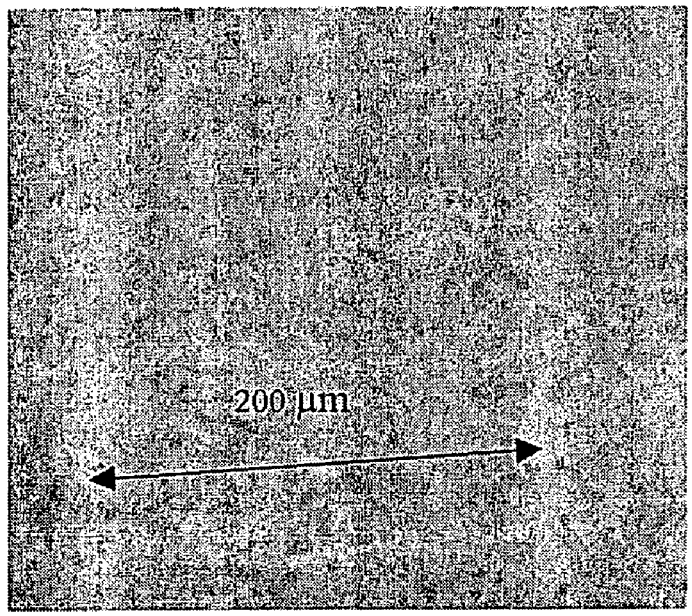
FIGS. 18 and 19 are microscopic images of emulsions made in Example 1.
Figure 19:
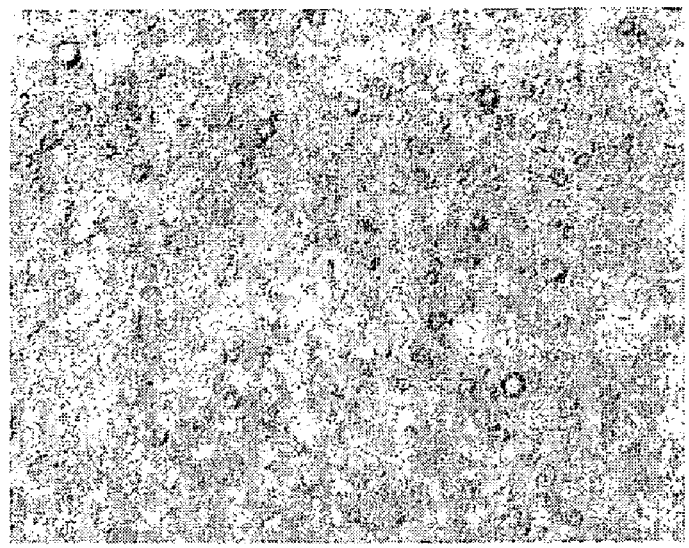

FIGS. 18 and 19 are microscopic images at a magnification of 100 for the foregoing emulsion for two different size ranges. FIG. 18. shows a droplet size from about 0.5 to about 2 microns using the heat treated porous substrate of pore size 0.5 micron at a First Liquid flow rate of 2.0 standard liters per minute (SLPM). FIG. 19 shows a droplet size from about 1 to about 8 microns using the heat treated porous substrate of pore size 0.5 micron at a First Liquid flow rate of 0.5 SLPM.

While the invention has been explained in relation to specific embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:
1. A process for making an emulsion, comprising:
flowing a first liquid in a process microchannel having a wall with an apertured section; and
flowing a second liquid through the apertured section into the process microchannel in contact with the first liquid to form the emulsion, the second liquid being immiscible with the first liquid, the first liquid forming a continuous phase, and the second liquid forming a discontinuous phase dispersed in the first liquid, the process microchannel having a narrowed height or width adjacent to the apertured section, the first liquid flowing through a region upstream of the apertured section having a height or width greater than the narrowed height or width adjacent to the apertured section, the emulsion flowing through a region downstream of the apertured section having a height or width greater than the narrowed height or width adjacent to the apertured section.

2. The process of claim 1 with the step of exchanging heat between the process microchannel and an adjacent heat exchanger.

3. The process of claim 2 wherein the heat exchanger comprises a heat exchange channels.

4. The process of claim 3 wherein the heat exchange channel comprises a microchannel having an internal dimension of width or height of up to about 10 mm.

5. The process of claim 3 wherein the heat exchange channel is made of a material comprising: steel; monel; inconel; aluminum; titanium; nickel; copper; brass; an alloy of any of the foregoing metals; a polymer; ceramics; glass; a composite comprising polymer and fiberglass; quartz; silicon; or a combination of two or more thereof.

6. The process of claim 1 wherein the apertured section comprises a sheet or plate with an array of apertures in the sheet or plate.

7. The process of claim 6 with a coating overlying at least part of the sheet or plate and filling part of the apertures.

8. The process of claim 6 wherein the sheet or plate is heat treated.

9. The process of claim 1 wherein the apertured section comprises a relatively thin sheet overlying a relatively thick sheet or plate, the relatively thin sheet containing an array of relatively small apertures, and the relatively thick sheet or plate containing an array of relatively large apertures, the relatively small apertures being coaxially aligned with the relatively large apertures.

10. The process of claim 1 wherein the apertured section has a wall thickness and a length along the flow path of the first liquid flowing through the process microchannel, the ratio of the wall thickness to the length along the flow path being from about 0.01 to about 1.

11. The process of claim 1 wherein the discontinuous phase is in the form of droplets having a mean diameter in the range of up to about 50 microns.

12. The process of claim 1 wherein the discontinuous phase comprises droplets having a mean diameter of up to about 50 microns, the standard deviation for the droplet size being from about 0.001 to about 10 microns.

13. The process of claim 1 wherein the first liquid comprises an organic liquid.

14. The process of claim 1 wherein the first liquid comprises an oil.

15. The process of claim 1 wherein the second liquid comprises water.

16. The process of claim 1 wherein the second liquid comprises an organic liquid.

17. The process of claim 1 wherein the second liquid comprises an oil.

18. The process of claim 1 wherein the first liquid comprises water.

19. The process of claim 1 wherein the process microchannel has an internal dimension of width or height of up to about 10 mm.

20. The process of claim 1 wherein the process microchannel is made of a material comprising: steel; monel; inconel; aluminum; titanium; nickel; copper; brass; an alloy of any of the foregoing metals; a polymer; ceramics; glass; a composite comprising a polymer and fiberglass; quartz; silicon; or a combination of two or more thereof.

21. The process of claim 1 wherein the emulsion is cooled to room temperature within a time period of up to about 10 minutes.

22. The process of claim 1 wherein the emulsion is filtered.

23. The process of claim 1 wherein the emulsion comprises a water-in-oil emulsion.

24. The process of claim 1 wherein the emulsion comprises an oil-in-water emulsion.

25. The process of claim 1 wherein either the first liquid or the second liquid comprises a natural oil, synthetic oil, or mixture thereof.

26. The process of claim 1 wherein either the first liquid or the second liquid comprises an organic liquid derived from a vegetable source, a mineral source, or mixture thereof.

27. The process of claim 1 wherein a surfactant is mixed with the first liquid, the second liquid, or both the first and second liquid.

28. The process of claim 27 wherein the surfactant comprises an alkanolamine, alkylaryl sulfonate, amine oxide, carboxylated alcohol ethoxylate, ethoxylated alcohol, ethoxylated alkyl phenol, ethoxylated amine, ethoxylated amide, ethoxylated fatty acid, ethoxylated fatty esters, ethoxylated fatty oil, fatty ester, glycerol ester, glycol ester, sorbitan ester, imidazoline derivative, lecithin, lecithin derivative, lignin, lignin derivative, monoglyceride, monoglyceride derivative, olefin sulfonate, phosphate ester, phosphate ester derivative, propoxylated fatty acid, ethoxylated fatty acid, propoxylated alcohol or alkyl phenol, ethoxylated alcohol or alkyl phenol, sorbitan derivative, sucrose ester, sulfonate of dodecyl ortridecyl benzene, naphthalene sulfonate, petroleum sulfonate, tridecyl or dodecyl benzene sulfonic acid, sulfosuccinate, sulfosuccinate derivative, or mixture of two or more thereof.

29. The process of claim 1 wherein the emulsion is a personal care product, a paint composition, an adhesive composition, a glue composition, a caulk composition, a sealant composition, a food composition, an agricultural composition, a pharmaceutical composition, or a fuel composition.

30. The process of claim 1 wherein the process is employed in an emulsion polymerization process.

31. A process for making an emulsion in an emulsion forming unit comprising a plurality of process microchannels and adjacent liquid channels, each process microchannel and adjacent liquid channel having a common wall, each process microchannel having at least one apertured section in the common wall, the process microchannels having narrowed widths or heights adjacent to the apertured sections, the process microchannels and liquid channels having rectangular cross sections and being aligned in side by side or stacked planes, comprising:

flowing a first liquid in the process microchannels; and flowing a second liquid from the liquid channels through the apertured sections into the process microchannels in contact with the first liquid, the second liquid being immiscible with the first liquid, the first liquid forming a continuous phase, and the second liquid forming a discontinuous phase dispersed in the first liquid.

* * * * *